US008309349B2

(12) United States Patent
Glorioso et al.

(10) Patent No.: US 8,309,349 B2
(45) Date of Patent: Nov. 13, 2012

(54) CELL LINE

(75) Inventors: Joseph C. Glorioso, Blawnox, PA (US); Darren Wolfe, Verona, PA (US); David Krisky, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 12/418,062

(22) Filed: Apr. 3, 2009

(65) Prior Publication Data

US 2009/0238807 A1    Sep. 24, 2009

Related U.S. Application Data

(60) Division of application No. 11/694,118, filed on Mar. 30, 2007, now Pat. No. 7,531,167, which is a division of application No. 11/261,389, filed on Oct. 28, 2005, and a continuation of application No. PCT/US2005/039162, filed on Oct. 28, 2005.

(60) Provisional application No. 60/622,889, filed on Oct. 28, 2004.

(51) Int. Cl.
*C12N 5/00*     (2006.01)
*C12N 15/00*    (2006.01)

(52) U.S. Cl. ........................... 435/325; 435/455

(58) Field of Classification Search .................. 435/325, 435/455
See application file for complete search history.

(56) References Cited

U.S. PATENT DOCUMENTS

| | | | |
|---|---|---|---|
| 5,804,413 | A | 9/1998 | DeLuca |
| 5,837,532 | A | 11/1998 | Preston et al. |
| 5,846,782 | A | 12/1998 | Wickham et al. |
| 5,849,572 | A | 12/1998 | Glorioso et al. |
| 5,869,040 | A | 2/1999 | Oin |
| 5,952,488 | A | 9/1999 | Matusik |
| 5,998,584 | A | 12/1999 | Baekkeskov et al. |
| 6,248,320 | B1 | 6/2001 | Coffin et al. |
| 6,696,423 | B1 | 2/2004 | Barsoum et al. |
| 6,780,409 | B2 | 8/2004 | During et al. |
| 6,821,753 | B2 * | 11/2004 | Coffin ........................ 435/69.1 |
| 7,262,033 | B1 * | 8/2007 | Coffin et al. ................ 435/91.4 |
| 2002/0091094 | A1 | 7/2002 | During et al. |
| 2005/0025746 | A1 | 2/2005 | During et al. |
| 2007/0178069 | A1 | 8/2007 | Glorioso et al. |

FOREIGN PATENT DOCUMENTS

| | | | |
|---|---|---|---|
| GB | WO 0008194 | * | 2/2000 |
| JP | 6-292569 A | | 10/1994 |
| JP | H11-507552 A | | 6/1999 |
| JP | 2002-506355 A | | 2/2002 |
| JP | 2002-526039 A | | 8/2002 |
| JP | 2003-506083 A | | 2/2003 |
| WO | WO 91/02788 A1 | | 3/1991 |
| WO | WO 96/04394 A1 | | 2/1996 |
| WO | 97/00326 A1 | | 1/1997 |
| WO | WO 98/15637 A1 | | 4/1998 |
| WO | WO 99/06583 A1 | | 2/1999 |
| WO | 99/53085 A2 | | 10/1999 |
| WO | 01/11034 A2 | | 2/2001 |
| WO | WO 01/82973 A2 | | 11/2001 |
| WO | WO 02/16420 A2 | | 2/2002 |
| WO | 2006/050211 A2 | | 5/2006 |

OTHER PUBLICATIONS

Liu (Mol. Therapy, Jul. 2004, vol. 10, No. 1, p. 57-66).*
Arafat et al., *Clinical Cancer Research*, 6(11): 4442-4448 (Nov. 2000).
Berkner, *BioTechniques*, 6(7): 616-629 (Jul./Aug. 1988).
Bu et al., *Proceedings of the National Academy of Science of the United States of America*, 89(6): 2115-2119 (Mar. 15, 1992).
Burton et al., *Stem Cells*, 19: 358-377 (2001).
Catheline et al., *Pain*, 92(3): 389-398 (Jun. 2001).
Chaplan et al., *Journal of Neuroscience Methods*, 53(1): 55-63 (Jul. 1994).
Chattopadhyay et al. *Annals of Neurology*, 51(1): 19-27 (Jan. 2002).
Chattopadhyay et al. *European Journal of Neuroscience*, 17(4): 732-740 (Feb. 2003).
Chattopadhyay et al., *Society for Neuroscience, Program* 413.8.2003: 1 (Oct. 1, 2003).
Chattopadhyay et al., Poster: "HSV-Mediated Transfer of VEGF Prevents Diabetic Neuropathy in the Mouse," presented at the annual meeting of the Society for Neuroscience, New Orleans, Louisiana, Nov. 8-12, 2003.
Chen et al., *Journal of Virology*, 74(21): 10132-10141 (Nov. 2000).
Coffin et al., "Herpes Simplex Virus-Based Vectors," *Genetic Manipulation of the Nervous System* (Latchman ed.), 99-114 (Academic Press, London, 1996).
Coffin et al., *Gene Therapy*, 3(10): 886-891 (Oct. 1996).
Deonarain, *Expert Opinion on Therapeutic Patents*, 8(1): 53-69 (1998).
Dixon, *Annual Review of Pharmacology and Toxicology*, 20: 441-462 (1980).
Glorioso et al., *Annual Review of Microbiology*, 58: 253-271 (2004).
Glorioso et al., *2nd International Symposium on Molecular Diagnostics & Skin Gene Therapy 2003*, 39 (Mar. 27-29, 2003).
Goncalves, *BioEssays*, 27(5): 506-517 (2005).
Gorecki, *Expert Opinion Emerging Drugs*, 6(2): 187-198 (2001).
Goss et al. *Diabetes*, 51(7): 2227-2232 (Jul. 2002). Goss et al., *Society for Neuroscience, Program* No. 437.7.2003: 1 (Oct. 1, 2003).
Goss et al., "Delivery of Herpes Simplex Virus-Based Vectors to the Nervous System," *Gene Delivery to Mammalian Cells*, (Ed. William C. Heiser) 2: 309-322 (Humana Press, Totowa 2004).
Goss et al., *Annals of Neurology*, 52(5): 662-665 (Nov. 2002).
Goss et al., *Gene Therapy*, 8(7): 551-556 (Apr. 2001).
Goss et al., Poster: "HSV Vector Gene Transfer of IL-4, TNF-Soluble Receptor, or GAD Reduces Pain-Related Behavior in a Mouse Model of Bone Cancer," presented at the annual meeting of the Society for Neuroscience, New Orleans, Louisiana, Nov. 10, 2003.
Gupta et al., *Nature*, 442: 82-85, (Jul. 6, 2006).
Hadjipanayis et al., *Cancer Research*, 65(12): 5310-5316 (Jun. 15, 2005).
Hao et al. *Molecular Therapy*, 8(3): 367-375 (Sep. 2003).
Hao et al., *Annals of Neurology*, 57(6): 914-918 (Jun. 2005).

(Continued)

*Primary Examiner* — Michael C. Wilson
(74) *Attorney, Agent, or Firm* — Leydig, Voit & Mayer, Ltd.

(57) ABSTRACT

The invention provides a cell line complementing HSV ICP4, ICP27, and UL55 genes.

3 Claims, 17 Drawing Sheets

OTHER PUBLICATIONS

Hao et al., *Society for Neuroscience, Program* No. 131.8.2003: 1 (Oct. 1, 2003).
Hao et al., *Pain*, 102(1-2): 135-142 (Mar. 2003).
Hargreaves et al., *Pain*, 32: 77-88 (1988).
Jaffe et al., *Clinical Research*, 39(2): 302A (Apr. 1991).
Jasmin et al., *Nature*, 424(6946): 316-320 (Jul. 17, 2003).
Jin et al., *Journal of Virology*, 77(11): 6556-6561 (Jun. 2003).
Johnson-Saliba et al., *Current Drugs Targets*, 2(4): 371-399 (2001).
Kang et al., *Virology*, 312: 233-244 (2003).
Krisky et al, "Development of Replication-Defective Herpes Simplex Virus Vectors," *Gene Therapy Protocols*, (Robbins, Ed., Humana Press, Totowa, New Jersey), 79-102 (1997).
Ladunga, *Current Opinion in Biotechnology*, 11(1): 13-18 (Feb. 2000).
Liu et al., *Society for Neuroscience, Program* No. 437.8.2003: 1 (Nov. 2003).
Liu et al., *Journal of Neurochemistry*, 67(4): 1457-1462 (Oct. 1996).
Liu et al., *Molecular Therapy*, 10(1): 57-66 (Jul. 2004).
Liu et al., Poster: "Peripherally Delivered Glutamic Acid Decarboxylase Gene Therapy for Spinal Cord Injury Pain Peripherally Delivered Glutamic Acid Decarboxylase Gene Therapy for Spinal Cord Injury Pain," presented at the annual meeting of the Society for Neuroscience, New Orleans, Louisiana, Nov. 8-12, 2003.
Luo et al., *Science*, 298(5592): 425-429 (Oct. 11, 2002).
Mata et al., *Society for Neuroscience, Program* No. 775.4.2003: 1 (Oct. 1, 2003).
Mata et al., *Experimental Neurology*, 184: S25-S29 (2003).
Mata et al., Poster: "Gene Therapy for Spinal Cord Hemisection Using a Replication Incompetent HSV-Based Vector to Deliver the Glial Cell Derived Neurotrophic Factor (GDNF)," Presented at the annual meeting of the Society for Neuroscience, New Orleans, Louisiana, Nov. 8-12, 2003.
NCBI, "Glutamate Decarboxylase 1 Isoform GAD67; Glutamate Decarboxylase 1 (Brain, 67kD) [*Homo sapiens*]," Database Entrez-Nucleotide, Accession No. NM-000808 (Aug. 23, 2004). Retrieved on Oct. 26, 2004.
NCBI, "*Homo sapiens* Glutamate Decarboxylase 1 (Brain, 67kDa) (GAD1), Transcript Variant GAD67, mRNA," Database Entrez-Nucleotide, Accession No. NM-000817 (Aug. 23, 2004). Retrieved on Oct. 26, 2004.
NCBI, "*Homo sapiens* Proenkephalin (PENK), mRNA," Database Entrez-Nucleotide, Accession No. NM_006211 (Oct. 14, 2005). Retrieved on Apr. 28, 2006.
NCBI, "Human Herpesvirus 1, Complete Genome," Database Entrez-Nucleotide, Accession No. NC_001806 (Apr. 7, 2006). Retrieved on May 1, 2006.
Negus et al., *The Jour. of Pharm. and Expt. Ther.*, 319(2):507-514 (2006).
Niranjan et al, *Molecular Therapy*, 8(4): 530-542 (Oct. 2003).
Peng et al., *Journal of NeuroVirology*, 14: 41-52 (2008).
Pradat et al., *Human Gene Therapy*, 12(18): 2237-2249 (Dec. 10, 2001).
Rosenfeld et al., *Science*, 252(5004): 431-434 (Apr. 19, 1991).
Rosenfeld et al., *Clinical Research*, 39(2): 311A (Apr. 1991).
Shoji et al., *Current Pharmaceutical Design*, 10(7): 785-796 (2004).
Verdu et al., *Muscle & Nerve* 22(3): 329-340 (Mar. 1999).
Verma et al., *Annual Review of Biochemistry*, 74: 711-738 (2005).
Verma et al., *Nature*, 389: 239-242 (Sep. 19, 1997).
Wagner et al., *Proceedings of the National Academy of Sciences of the United States of America*, 78(3): 1441-1445 (Mar. 1981).
Wolfe et al., *Gene Therapy*, 11(23): 1675-1684 (Dec. 2004).
International Preliminary Report on Patentability dated Mar. 21, 2007 in PCT/US05/39162.
International Search Report dated Aug. 30, 2006, in PCT/US05/39162.
Prosecution History of U.S. Patent Application history of U.S. Appl. No. 11/261,389 between Jul. 1, 2008 and Dec. 4, 2008.
Prosecution history of U.S. Appl. No. 11/261,389, filed Oct. 28, 2005, current as of Feb. 19, 2008.
Prosecution history of U.S. Appl. No. 11/261,389, filed Oct. 28, 2005, current as of Jul. 1, 2008.
Liu et al., *Society for Neuroscience, Program* No. 437.8.2003: 1 (Oct. 1, 2003).
Prosecution history of U.S. Appl. No. 11/261,389, current as of Feb. 5, 2010.
Prosecution history of U.S. Patent 7,531,167, current as of Feb. 5, 2010.
Nash et al., *Virology*, 204: 794-798 (1994).
Prosecution History of U.S. Appl. No. 11/261,389 from Feb. 6, 2010 through Jul. 2, 2010.
Australian Patent Office, Examination Report in Australian Patent Application No. 2005302408 (Dec. 10, 2010).
Jasmin et al., "Adenovirus-mediated Expression of GAD65 into the Trigeminal Ganglion Produces Long-lasting Analgesia," *Neurosurgery*, 62(6): (Abstract No. 883), 1427 (Jun. 2008).
Lee et al., "Vector-Mediated Gene Transfer to Express Inhibitory Neurotransmitters in Dorsal Root Ganglion Reduces Pain in a Rodent Model of Lumbar Radiculopathy," *Spine*, 31(14): 1555-1558 (2006).
Lee et al., "Constitutive GABA expression via a recombinant adeno-associated virus consistently attenuates neuropathic pain," *Biochemical and Biophysical Research Communications*, 357: 971-976 (2007).
Lenz et al., "Reorganization of Sensory Modalities Evoked by Microstimulation in Region of the Thalamic Principal Sensory Nucleus in Patients With Pain Due to Nervous System Injury," *The Journal of Comparative Neurology*, 399: 125-138 (1998).
Liu et al., "Release of GABA from sensory neurons transduced with a GAD67—expressing vector occurs by non-vesicular mechanisms," *Brain Research*, 1073-1074: 297-304 (2006).
Liu et al., "A novel human foamy virus mediated gene transfer of GAD67 reduces neuropathic pain following spinal cord injury," *Neuroscience Letters*, 432: 13-18 (2008).
Miyazato et al., "Herpes simplex virus vector-mediated gene delivery of glutamic acid decarboxylase reduces detrusor overactivity in spinal cord-injured rats," *Gene Therapy*, 1-9 (2009).
Pacchetti et al., "'Off' painful dystonia in Parkinson's disease treated with botulinum toxin," *Mov. Disord*. 10(3): (Abstract), 333-336 (May 1995).
Quintero-Wolfe et al., "Intrathecal Transplantation of the Human NeUronal GABA/Glycinergic hNT2.17 Cell Line for Alleviation of Neuropathic Pain in the Streptozotocin Model of Diabetic Neuropathy," *Neurosurgery*, 62(6): (Abstract No. 881), 1427 (Jun. 2008).
Selden et al., "α2-Noradrenergic Antagonist Administration into the Central Nucleus of the Amygdala Blocks Stress-induced Analgesia," *Neurosurgery*, 62(6): (Abstract No. 882), 1427 (Jun. 2008).
Prosecution history of U.S. Patent No. 7,531,167, current from Feb. 5, 2010 to Nov. 16, 2010.
Prosecution history of U.S. Appl. No. 11/261,389, filed Oct. 28, 2005, current from Jul. 2, 2010 to Nov. 16, 2010.
European Patent Office, Examination Report in European Patent Application No. 05 818 233.8 (Jun. 3, 2009).
Chinese Patent Office, Examination Report in Chinese Patent Application No. 200580044783.2 (Apr. 13, 2010) English Translation.
Goins et al., "Construction of Replication-Defective Herpes Simplex Virus Vectors," Current Protocols in Human Genetics, (Supplement 33): 12.11 1-12, 11,30 (2002).
Japanese Patent Office, Examination Report in Japanese Patent Application No. 2007/539217 (Jun. 21, 2011).
European Patent Office, Examination Report in European Patent Application No. 05 818 233.8 (May 23, 2011).
India Patent Office, Examination Report in Indian Patent Application No. 3468/DELNP/2007 (May 19, 2011).
JAPANESE PATENT OFFICE, Examination Report in Japanese Patent Application No. 539217/2007 (Feb. 21, 2012).
McGeoch et al., "The Complete DNA Sequence of the Long Unique Region in the Genome of Herpes Simplex Virus Type 1," *Journal of General Virology*, 69(7): 1531-1574 (Jul. 1988).
Prosecution history of U.S. Appl. No. 11/261,389, filed Oct. 28, 2005, current from Feb. 27, 2012 to Apr. 23, 2012.
AUSTRALIAN PATENT OFFICE, Examination Report in Australian Patent Application No. 2005302408 (Mar. 27, 2012).
AUSTRALIAN Patent Office, Examination Report in Australian Patent Application No. 2005302408 (Jun. 8, 2012).

EUROPEAN Patent Office, Examination Report in European Patent Application No. 11 169 442.8 (May 30, 2012).

Prosecution history of U.S. Appl. No. 11/261,389, filed Oct. 28, 2005, current from Apr. 23, 2012 to Jun. 2012.

CHINESE PATENT OFFICE, Examination Report in Chinese Patent Application 200580044783.2 (May 17, 2012).

INDIAN Patent Office, Hearing Notice in reference of Indian Patent Application No. 3468/DELNP/2007 (Aug. 8, 2012).

Braak et al., "Parkinson's disease: lesions in dorsal horn layer 1, involvement of parasympathetic and sympathetic pre- and postganglionic neurons," *Acta Neuropathol*, 113: 421-429 (2007).

Dauer et al., "Parkinson's Disease: Mechanisms and Models," *Neuron*, 39: 889-909 (Sep. 11, 2003).

Ford, "Pain in Parkinson's Disease," *Movement Disorders*, 25(Supp. 1): S98-S103 (2010).

Goetz et al., "Pain in Parkinson's Disease," *Movement Disorders*, 1(1): 45-49 (1986).

Takeda et al., "Parkinson's disease with involvement of the parasympathetic ganglia," *Acta. Neuropathol.*, 86: 397-398 (1993).

Prosecution history of U.S. Appl. No. 11/261,389, filed Oct. 28, 2005, current from Nov. 16, 2010 to Feb. 27, 2012.

EUROPEAN PATENT OFFICE, Examination Report in European Patent Application No. 11 16 9442 (Sep. 21, 2011).

AUSTRALIAN PATENT OFFICE, Examination Report in Australian Patent Application No. 2005302408 (Feb. 14, 2012).

CHINESE PATENT OFFICE, Examination Report in Chinese Patent Application 200580044783.2 (Nov. 25, 2011).

\* cited by examiner

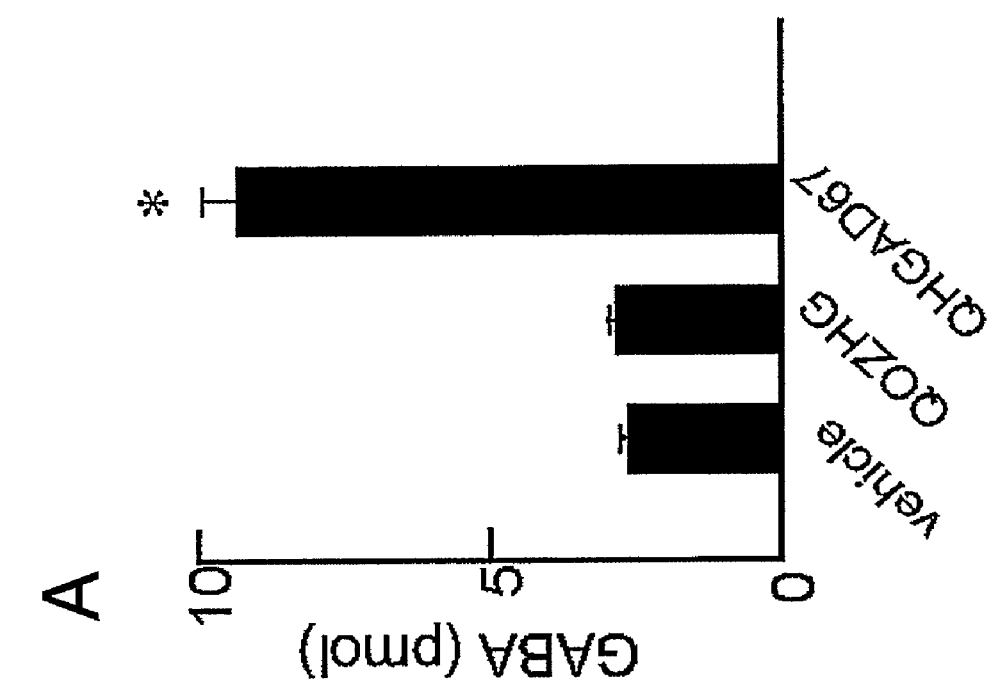
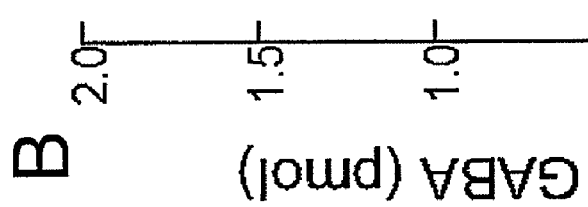
FIG. 4

FIG. 8

```
   1  gaattcttcg taggaattat cttttccctc ctctcacccg acagcctgcc tatttccaaa
  61  ggaaaaaaaa aaagcgtgtt gagtacgttc tggattactc ataagacctt ttttttttcc
 121  ttccgggcgc aaaaccgtga gctggattta taatcgccct ataaagctcc agaggcggtc
 181  aggcacctgc agaggagccc cgccgctccg ccgactagct gccccgcgca gcaacggcct
 241  cgtgatttcc ccgccgatcc ggtccccgcc tccccactct gccccgcct accccggagc
 301  cgtgcagccg cctctccgaa tctctctctt ctcctggcgc tcgcgtgcga gagggaacta
 361  gcgagaacga ggaagcagct ggaggtgacg ccgggcagat tacgcctgtc agggccgagc
 421  cgagcggatc gctgggcgct gtgcagagga aaggcgggag tgcccggctc gctgtcgcag
 481  agccgagcct gtttctgcgc cggaccagtc gaggactctg acagtagag gccccgggac
 541  gaccgagctg atggcgtctt cgacccatc ttcgtccgca acctcctcga acgcgggagc
 601  ggaccccaat accactaacc tgcgcccac aacgtacgat acctggtgcg gcgtggccca
 661  tggatgcacc agaaactgg ggctcaagat ctgcggcttc ttgcaaagga ccaacagcct
 721  ggaagagaag agtcgccttg tgagtgcctt cagggagagg caatcctcca agaacctgct
 781  ttcctgtgaa acagcgacc gggatgcccg cttccggcgc acagagactg acttctctaa
 841  tctgtttgct agagatctgc ttccggctaa gaacggtgag gagcaaaccg tgcaattcct
 901  cctggaagtg gtggacatac tcctcaacta tgtccgcaag acatttgatc gctccaccaa
 961  ggtgctggac tttcatcacc cacaccagtt gctggaaggc atggagggct tcaacttgga
1021  gctctctgac cacccgagt ccctggagca gatcctggtt gactgcagag acaccttgaa
1081  gtatgggtt cgcacaggtc atcctcgatt tttcaaccag ctctccactg gattggatat
1141  tattggccta gctggagaat ggctgacatc aacggccaat accaacatgt ttacatatga
1201  aattgcacca gtgtttgtcc tcatggaaca aataacactt aagaagatga gagagatagt
1261  tggatggtca agtaaagatg gtgatgggat attttctcct ggggcgcca tatccaacat
1321  gtacagcatc atggctgctc gctacaagta cttcccggaa gttaagacaa agggcatggc
1381  ggctgtgcct aaactggtcc tcttcacctc agaacagagt cactattcca taaagaaagc
1441  tggggctgca cttggctttg gaactgacaa tgtgattttg ataaagtgca atgaaagggg
1501  gaaaataatt ccagctgatt tgaggcaaa aattcttgaa gccaaacaga agggatatgt
1561  tccctttat gtcaatgcaa ctgctggcac gactgtttat ggagcttttg atccgataca
1621  agagattgca gatatatgtg agaaatataa cctttggttg catgtcgatg ctgcctgggg
1681  aggtgggctg tcatgtcca ggaagcaccg ccataaactc aacggcatag aaagggccaa
1741  ctcagtcacc tggaaccctc acaagatgat gggcgtgctg ttgcagtgct ctgccattct
1801  cgtcaaggaa aagggtatac tccaaggatg caaccagatg tgtgcaggat atctcttcca
1861  gccagacaag cagtatgatg tctcctacga caccggggac aaggcaattc agtgtggccg
1921  ccacgtggat atcttcaagt tctggctgat gtggaaagca aagggcacag tgggatttga
1981  aaaccagatc aacaaatgcc tggaactggc tgaataccct tatgccaaga ttaaaaacag
2041  agaagaattt gagatggttt tcaatggcga gcctgagcac acaaacgtct gttttggta
2101  tattccacaa agcctcaggg gtgtgccaga cagccctcaa cgacgggaaa agctacacaa
2161  ggtggctcca aaaatcaaag ccctgatgat ggagtcaggt acgaccatgg ttggctacca
2221  gccccaaggg gacaaggcca acttcttccg gatggtcatc tccaacccag ccgctaccca
2281  gtctgacatt gacttcctca ttgaggagat agaaaagactg gccaggatc tgtaatcatc
2341  cttcgcagaa catgagttta tgggaatgcc ttttcccctct ggcactccag aacaaacctc
2401  tatatgttgc tgaaacacac aggccatttc attgagggaa aacataatat cttgaagaat
2461  attgttaaaa ccttacttaa agcttgtttg ttctagttag caggaaatag tgttctttt
2521  aaaaagttgc acattaggaa cagagtatat atgtacagtt atacatacct ctctctatat
2581  atacatgtat agtgagtgtg cttagtaat agatcacggc atgtttccg ctccaagaga
2641  attcacttta ccttcagcag ttaccgagga gctaaacatg ctgccaacca gcttgtccaa
2701  caactccagg aaaactgttt ttcaaaacgc catgtcctag gggccaaggg aaatgctgtt
2761  ggtgagaatc gacctcactg tcagcgtttc tccacctgaa gtgatgatgg atgagaaaaa
2821  acaccaccaa atgacaagtc acaccctccc cattagtatc ctgttagggg aaaatagtag
2881  cagagtcatt gttacaggtg tactatggct gtattttaga gattaatttg tgtagattgt
2941  gtaaattcct gttgtctgac cttggtggtg ggagggaga ctatgtgtca tgatttcaat
3001  gattgtttaa ttgtaggtca atgaaatatt tgcttattta tattcagaga tgtaccatgt
3061  taaagaggcg tcttgtattt tcttcccatt tgtaatgtat cttatttata tatgaagtaa
3121  gttctgaaaa ctgtttatgg tattttcgtg catttgtgag ccaaagagaa aagattaaaa
3181  ttagtgagat ttgtatttat attagagtgc ccttaaaata atgatttaag cattttactg
3241  tctgtaagag aattctaaga ttgtacatga cataagttat agtaatcatg gcaaatcctg
3301  ttacttaaat agcatctgct cttctcttac gctctctgtc tggctgtacg tctggtgttc
3361  tcaatgcttt tctagcaact gttggataat aactagatct cctgtaattt tgtagtagtt
3421  gatgaccaat ctctgtgact cgcttagctg aaacctaagg caacatttcc gaagaccttc
3481  tgaagatctc agataaagtg accaggctca caactgtttt tgaagaaggg aaattcacac
3541  tgtgcgtttt gagtatgcaa gaagaatata aataaataaa atatctcatg gagattgaca
3601  aaaaaaaaa  (SEQ ID NO:1)
```

FIG. 9

```
  1  masstpsssa tssnagadpn ttnlrpttyd twcgvahgct rklglkicgf lqrtnsleek
 61  srlvsafrer qssknllsce nsdrdarfrr tetdfsnlfa rdllpaknge eqtvqfllev
121  vdillnyvrk tfdrstkvld fhhphqlleg megfnlelsd hpesleqilv dcrdtlkygv
181  rtghprffnq lstgldiigl agewltstan tnmftyeiap vfvlmeqitl kkmreivgws
241  skdgdgifsp ggaisnmysi maarykyfpe vktkgmaavp klvlftseqs hysikkagaa
301  lgfgtdnvil ikcnergkii padfeakile akqkgyvpfy vnatagttvy gafdpiqeia
361  dicekynlwl hvdaawgggl lmsrkhrhkl ngieransvt wnphkmmgvl lqcsailvke
421  kgilqgcnqm cagylfqpdk qydvsydtgd kaiqcgrhvd ifkfwlmwka kgtvgfenqi
481  nkclelaeyl yakiknreef emvfngepeh tnvcfwyipq slrgvpdspq rreklhkvap
541  kikalmmesg ttmvgyqpqg dkanffrmvi snpaatqsdi dflieeierl gqdl
(SEQ ID NO:2)
```

FIG. 10

SEQ ID NO: 3   GCGGGAGCGGATCCTAATA

SEQ ID NO: 4   TGGTGCATCCATGGGCTAC

SEQ ID NO: 5   CGTCCTACAACATATGATACTTGGTGTG

SEQ ID NO: 6   CCGAGGGCCCACTAAAGG

SEQ ID NO: 7   TGCTGTTGAAGTCACAGGAGA

SEQ ID NO: 8   CATCCTGGGCTACACTGAGGACCA

SEQUENCE LISTING

<160> NUMBER OF SEQ ID NOS: 9

<210> SEQ ID NO 1
<211> LENGTH: 3610
<212> TYPE: DNA

<213> ORGANISM: Homo Sapiens

<400> SEQUENCE: 1

```
gaattcttcg taggaattat cttttccctc ctctcacccg acagcctgcc tatttccaaa      60
ggaaaaaaaa aaagcgtgtt gagtacgttc tggattactc ataagacctt ttttttttcc     120
ttccgggcgc aaaaccgtga gctggattta taatcgccct ataaagctcc agaggcggtc     180
aggcacctgc agaggagccc cgccgctccg ccgactagct gccccgcgca gcaacggcct     240
cgtgatttcc ccgccgatcc ggtccccgcc tccccactct gccccgcct acccccggagc     300
cgtgcagccg cctctccgaa tctctctctt tcctggcgc tcgcgtgcga gagggaacta     360
gcgagaacga ggaagcagct ggaggtgacg ccgggcagat tacgcctgtc agggccgagc     420
cgagcggatc gctgggcgct gtgcagagga aggcgggag tgcccggctc gctgtcgcag     480
agccgagcct gtttctgcgc cggaccagtc gaggactctg acagtagag gccccgggac     540
gaccgagctg atggcgtctt cgaccccatc ttcgtccgca acctcctcga acgcgggagc     600
ggaccccaat accactaacc tgcgccccac aacgtacgat acctggtgcg cgtggcccca     660
tggatgcacc agaaaactgg ggctcaagat ctgcggcttc ttgcaaagga ccaacagcct     720
ggaagagaag agtcgccttg tgagtgcctt cagggagagg caatcctcca agaacctgct     780
ttcctgtgaa acagcgacc gggatgcccg cttccggcgc acagagactg acttctctaa     840
tctgtttgct agagatctgc ttccggctaa gaacggtgag gagcaaaccg tgcaattcct     900
cctggaagtg gtggacatac tcctcaacta tgtccgcaag acatttgatc gctccaccaa     960
ggtgctggac tttcatcacc cacaccagtt gctggaaggc atggagggct tcaacttgga    1020
gctctctgac cacccccgagt ccctgggagca gatcctggtt gactgcagag acaccttgaa    1080
gtatggggtt cgcacaggtc atcctcgatt tttcaaccag ctctccactg gattggatat    1140
tattggccta gctggagaat ggctgacatc aacggccaat accacatgt ttacatatga    1200
aattgcacca gtgtttgtcc tcatggaaca ataacactt aagaagatga gagagatagt    1260
tggatggtca agtaaagatg gtgatgggat attttctcct gggggcgcca tatccaacat    1320
gtacagcatc atggctgctc gctacaagta cttcccggaa gttaagacaa agggcatggc    1380
ggctgtgcct aaactggtcc tcttcacctc agaacagagt cactattcca taaagaaagc    1440
tggggctgca cttggctttg gaactgacaa tgtgattttg ataaagtgca atgaaagggg    1500
gaaaataatt ccagctgatt tgaggcaaa aattcttgaa gccaaacaga agggatatgt    1560
tcccttttat gtcaatgcaa ctgctggcac gactgtttat ggagcttttg atccgataca    1620
agagattgca gatatatgtg agaaatataa ccttttggttg catgtcgatg ctgcctgggg    1680
aggtgggctc tcatgtccta ggaagcaccg ccataaactc aacggcatag aaagggccaa    1740
ctcagtcacc tggaacctc acaagatgat gggcgtgctg ttgcagtgct ctgccattct    1800
cgtcaaggaa aagggtatac tccaaggatg caaccagatg tgtgcaggat atctcttcca    1860
gccagacaag cagtatgatg tctcctacga caccgggac aaggcaattc agtgtggccg    1920
ccacgtggat atcttcaagt tctggctgat gtggaaagca aagggcacag tgggatttga    1980
aaaccagatc aacaaatgcc tggaactggc tgaatacctc tatgccaaga ttaaaaacag    2040
agaagaattt gagatggttt tcaatggcga gcctgagcac acaaacgtct gttttggta    2100
tattccacaa agcctcaggg gtgtgccaga cagccctcaa cgacgggaaa agctacacaa    2160
ggtggctcca aaaatcaaag ccctgatgat ggagtcaggt acgaccatgg ttggctacca    2220
gccccaaggg gacaaggcca acttcttccg gatggtcatc tccaacccag ccgctaccca    2280
```

-continued

```
gtctgacatt gacttcctca ttgaggagat agaaagactg ggccaggatc tgtaatcatc    2340
cttcgcagaa catgagttta tgggaatgcc ttttccctct ggcactccag aacaaacctc    2400
tatatgttgc tgaaacacac aggccatttc attgagggaa acataatat  cttgaagaat    2460
attgttaaaa ccttacttaa agcttgtttg ttctagttag caggaaatag tgttctttt    2520
aaaaagttgc acattaggaa cagagtatat atgtacagtt atacatacct ctctctatat    2580
atacatgtat agtgagtgtg gcttagtaat agatcacggc atgtttcccg ctccaagaga    2640
attcacttta ccttcagcag ttaccgagga gctaaacatg ctgccaacca gcttgtccaa    2700
caactccagg aaaactgttt ttcaaaacgc catgtcctag gggccaaggg aaatgctgtt    2760
ggtgagaatc gacctcactg tcagcgtttc tccacctgaa gtgatgatgg atgagaaaaa    2820
acaccaccaa atgacaagtc acaccctccc cattagtatc ctgttagggg aaaatagtag    2880
cagagtcatt gttacaggtg tactatggct gtattttaga gattaatttg tgtagattgt    2940
gtaaattcct gttgtctgac cttggtggtg ggagggggaga ctatgtgtca tgatttcaat   3000
gattgtttaa ttgtaggtca atgaaatatt tgcttattta tattcagaga tgtaccatgt    3060
taaagaggcg tcttgtattt tcttcccatt tgtaatgtat cttatttata tatgaagtaa    3120
gttctgaaaa ctgtttatgg tattttcgtg catttgtgag ccaaagagaa aagattaaaa    3180
ttagtgagat ttgtatttat attagagtgc ccttaaaata atgatttaag cattttactg    3240
tctgtaagag aattctaaga ttgtacatga cataagttat agtaatcatg gcaaatcctg    3300
ttacttaaat agcatctgct cttctcttac gctctctgtc tggctgtacg tctggtgttc    3360
tcaatgcttt tctagcaact gttggataat aactagatct cctgtaattt tgtagtagtt    3420
gatgaccaat ctctgtgact cgcttagctg aaacctaagg caacatttcc gaagaccttc    3480
tgaagatctc agataaagtg accaggctca caactgtttt tgaagaaggg aaattcacac    3540
tgtgcgtttt gagtatgcaa gaagaatata aataaataaa atatctcatg gagattgaca    3600
aaaaaaaaaa                                                           3610
```

<210> SEQ ID NO 2
<211> LENGTH: 594
<212> TYPE: PRT
<213> ORGANISM: Homo sapiens

<400> SEQUENCE: 2

```
Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
            35                  40                  45

Gly Phe Leu Gln Arg Thr Asn Ser Leu Glu Glu Lys Ser Arg Leu Val
        50                  55                  60

Ser Ala Phe Arg Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140
```

```
His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
            165                 170                 175

Lys Tyr Gly Val Arg Thr Gly His Pro Arg Phe Phe Asn Gln Leu Ser
        180                 185                 190

Thr Gly Leu Asp Ile Ile Gly Leu Ala Gly Glu Trp Leu Thr Ser Thr
    195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
            245                 250                 255

Met Tyr Ser Ile Met Ala Ala Arg Tyr Lys Tyr Phe Pro Glu Val Lys
        260                 265                 270

Thr Lys Gly Met Ala Ala Val Pro Lys Leu Val Leu Phe Thr Ser Glu
    275                 280                 285

Gln Ser His Tyr Ser Ile Lys Lys Ala Gly Ala Ala Leu Gly Phe Gly
290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
            325                 330                 335

Val Pro Phe Tyr Val Asn Ala Thr Ala Gly Thr Thr Val Tyr Gly Ala
        340                 345                 350

Phe Asp Pro Ile Gln Glu Ile Ala Asp Ile Cys Glu Lys Tyr Asn Leu
    355                 360                 365

Trp Leu His Val Asp Ala Ala Trp Gly Gly Gly Leu Leu Met Ser Arg
370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
            405                 410                 415

Leu Val Lys Glu Lys Gly Ile Leu Gln Gly Cys Asn Gln Met Cys Ala
        420                 425                 430

Gly Tyr Leu Phe Gln Pro Asp Lys Gln Tyr Asp Val Ser Tyr Asp Thr
    435                 440                 445

Gly Asp Lys Ala Ile Gln Cys Gly Arg His Val Asp Ile Phe Lys Phe
450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
            485                 490                 495

Arg Glu Glu Phe Glu Met Val Phe Asn Gly Glu Pro Glu His Thr Asn
        500                 505                 510

Val Cys Phe Trp Tyr Ile Pro Gln Ser Leu Arg Gly Val Pro Asp Ser
    515                 520                 525

Pro Gln Arg Arg Glu Lys Leu His Lys Val Ala Pro Lys Ile Lys Ala
530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
```

```
                565                 570                 575
Gln Ser Asp Ile Asp Phe Leu Ile Glu Glu Ile Glu Arg Leu Gly Gln
            580                 585                 590

Asp Leu

<210> SEQ ID NO 3
<211> LENGTH: 19
<212> TYPE: DNA
<213> ORGANISM: Artificial
<220> FEATURE:
<223> OTHER INFORMATION: Forward primer

<400> SEQUENCE: 3
gcgggagcgg atcctaata                                             19

<210> SEQ ID NO 4
<211> LENGTH: 19
<212> TYPE: DNA
<213> ORGANISM: Artificial
<220> FEATURE:
<223> OTHER INFORMATION: Reverse primer

<400> SEQUENCE: 4
tggtgcatcc atgggctac                                             19

<210> SEQ ID NO 5
<211> LENGTH: 28
<212> TYPE: DNA
<213> ORGANISM: Artificial
<220> FEATURE:
<223> OTHER INFORMATION: probe

<400> SEQUENCE: 5
cgtcctacaa catatgatac ttggtgtg                                   28

<210> SEQ ID NO 6
<211> LENGTH: 18
<212> TYPE: DNA
<213> ORGANISM: Artificial
<220> FEATURE:
<223> OTHER INFORMATION: Forward primer

<400> SEQUENCE: 6
ccgagggccc actaaagg                                              18

<210> SEQ ID NO 7
<211> LENGTH: 21
<212> TYPE: DNA
<213> ORGANISM: Artificial
<220> FEATURE:
<223> OTHER INFORMATION: Reverse primer

<400> SEQUENCE: 7
tgctgttgaa gtcacaggag a                                          21

<210> SEQ ID NO 8
<211> LENGTH: 24
<212> TYPE: DNA
<213> ORGANISM: Artificial
<220> FEATURE:
<223> OTHER INFORMATION: Probe

<400> SEQUENCE: 8
catcctgggc tacactgagg acca                                       24
```

-continued

```
<210> SEQ ID NO 9
<211> LENGTH: 1239
<212> TYPE: DNA
<213> ORGANISM: Homo sapiens

<400> SEQUENCE: 9
cggcgagggt cctgccgagg gacccgttct gcgcccaggc aggctcgaag cacgcgtccc      60
tctctcctcg cagtccatgg cgcggttcct gacactttgc acttggctgc tgttgctcgg     120
ccccgggctc ctggcgaccg tgcgggccga atgcagccag gattgcgcga cgtgcagcta     180
ccgcctagtg cgcccggccg acatcaactt cctggcttgc gtaatggaat gtgaaggtaa     240
actgccttct ctgaaaattt gggaaacctg caaggagctc ctgcagctgt ccaaaccaga     300
gcttcctcaa gatggcacca gcaccctcag agaaaatagc aaaccggaag aaagccattt     360
gctagccaaa aggtatgggg gcttcatgaa aaggtatgga ggcttcatga agaaaatgga     420
tgagctttat cccatggagc cagaagaaga ggccaatgga agtgagatcc tcgccaagcg     480 gtatggggc ttcatgaaga aggatgcaga ggaggacgac tcgctggcca attcctcaga      540
cctgctaaaa gagcttctgg aaacagggga caaccgagag cgtagccacc accaggatgg     600
cagtgataat gaggaagaag tgagcaagag atatgggggc ttcatgagag gcttaaagag     660
aagcccccaa ctggaagatg aagccaaaga gctgcagaag cgatatgggg gcttcatgag     720
aagagtaggt cgcccagagt ggtggatgga ctaccagaaa cggtatggag gtttcctgaa     780
gcgctttgcc gaggctctgc cctccgacga agaaggcgaa agttactcca agaagttcc      840 tgaaatggaa aaaagatacg gaggatttat gagattttaa tattttccc actagtggcc       900 ccaggcccca gcaagcctcc ctccatcctc cagtgggaaa ctgttgatgg tgttttattg     960
tcatgtgttg cttgccttgt atagttgact tcattgtctg gataactata caacctgaaa    1020
actgtcattt caggttctgt gctcttttg gagtctttaa gctcagtatt agtctattgc     1080
agctatctcg ttttcatgct aaaatagttt ttgttatctt gtctcttatt tttgacaaac    1140
atcaataaat gcttacttgt atatagagat aataaaccta ttaccccaag tgcaaaaaaa    1200
aaaaaaaaaa aaaaaaaaaa aaaaaaaaaa aaaaaaaa                             1239
```

CELL LINE

CROSS-REFERENCE TO RELATED APPLICATIONS

This application is a divisional of U.S. patent application Ser. No. 11/694,118, filed Mar. 30, 2007, which issued on May 12, 2009 as U.S. Pat. No. 7,531,167 and which is a divisional of co-pending U.S. patent application Ser. No. 11/261,389, which was filed on Oct. 28, 2005, claiming the benefit of U.S. Provisional Patent Application 60/622,889, filed Oct. 28, 2004. U.S. patent application Ser. No. 11/694,118 also is a continuation of patent application PCT/US2005/39162, which was filed on Oct. 28, 2005, designating the Untied States and also claiming the benefit of U.S. Provisional Patent Application 60/622,889, filed Oct. 28, 2004. The contents of each of these applications are incorporated herein in their entireties.

STATEMENT REGARDING FEDERALLY SPONSORED RESEARCH AND DEVELOPMENT

This invention was made with Government support under Grant Numbers NS044507, NS38850 and NS43247, awarded by the United States National Institute of Neurological Disorders and Stroke. The Government has certain rights in the invention.

BRIEF SUMMARY OF THE INVENTION

The invention provides a cell line complementing HSV ICP4, ICP27, and UL55 genes.

BRIEF DESCRIPTION OF THE DRAWINGS

FIG. 4A is a representation of the amount of gamma amino butyric acid (GABA) released from primary DRG neurons transduced in vitro at an m.o.i. of 1 increased substantially in QHGAD67-infected compared to control or Q0ZHG-infected cells. GABA released over 5 min was determined by HPLC as described under Materials and Methods. The measurement of GABA concentration/well was performed three times and triplicate samples were used for each condition. Means±SEM, *$P<0.01$ vs. Q0HG or vehicle. FIG. 4B is a representation of the amount of GABA released from nerve terminals in spinal cord in vivo was determined by HPLC in microdialysate of dorsal horn. One week after subcutaneous inoculation of 30 μl of $1\times10^9$ pfu/ml QHGAD67 into one hind paw the amount of GABA (pmol/10 μl fraction of microdialysate) was substantially increased in QHGAD67-inoculated compared to control animals. Means±SEM, N=6, *$P<0.05$.

FIGS. 5A and 5B demonstrate that one week after hemisection there was a decrease in paw withdrawal threshold (mechanical allodynia), which persisted for 15 weeks as shown in vehicle-treated animals (x). Inoculation with QHGAD67 produced an antialiodynic effect reflected in an increased threshold value (open circle). Seven weeks after initial inoculation the antialiodnyic effect of QHGAD67 decreased, but reinoculation of QHGAD67 into the same animals reestablished the antinociceptive effect (*$P<0.05$, **$P<0.01$ vs. Q0ZHG-inoculated, N=6). (A) Ipsilateral and (B) contralateral to hemisection. FIGS. 5C and 5D demonstrate that one week after hemisection there was a significant decrease in paw withdrawal latency (thermal hyperalgesia) and injection of the vector resulted in a significant increase in paw withdrawal latency (open circles). By 7 weeks after initial inoculation both the antihyperalgesic effects of QHGAD67 had decreased, but reinoculation of QHGAD67 reestablished the antihyperalgesic effects (*$P<0.05$, **$P<0.01$ vs. Q0ZHG-inoculated, N=6. (C) Ipsilateral and (D) contralateral to hemisection. Q0ZHG-inoculated animals (open triangles) were indistinguishable from vehicle-treated controls in all cases (A-D).

FIG. 8 depicts SEQ ID NO:1 discussed herein.

FIG. 9 depicts SEQ ID NO:2 discussed herein.

FIG. 10 depicts SEQ ID NOs:3-8 discussed herein.

DETAILED DESCRIPTION OF THE INVENTION

Figure 1:
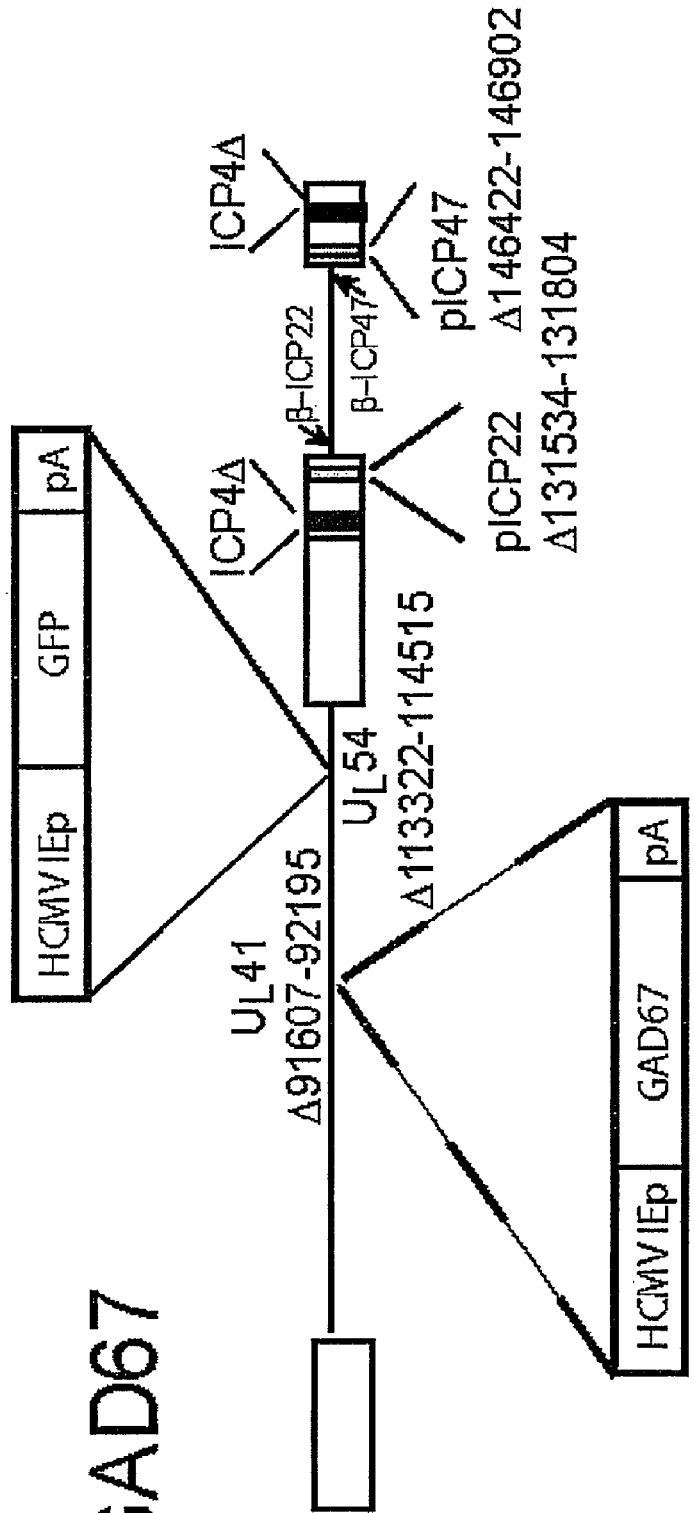
FIG. 1 is a schematic representation of exemplary vector constructs that can be used in the invention.
Figure 1:
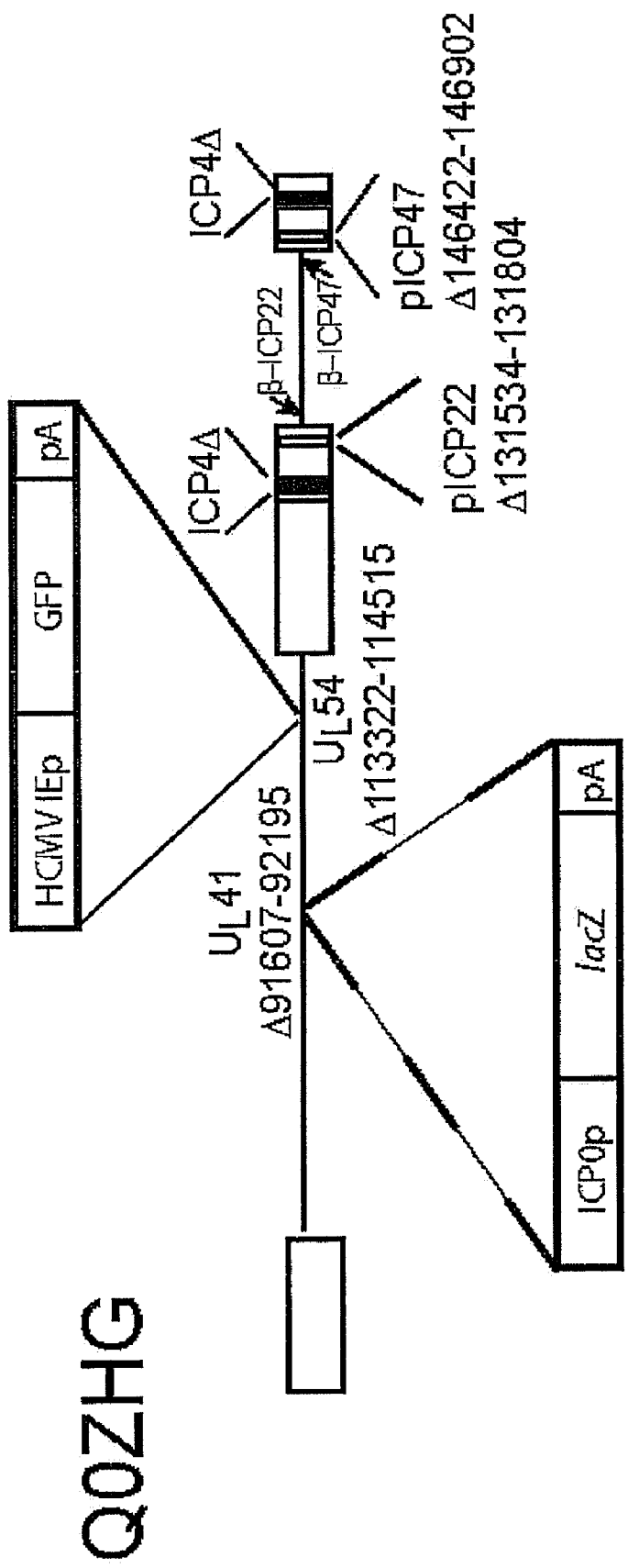

In one embodiment, the invention provides a vector comprising a polynucleotide sequence encoding a glutamic acid decarboxylase protein. The vector can be any suitable gene transfer vector. Examples of suitable vectors include plasmids, liposomes, molecular conjugates (e.g., transferrin), and viruses. Preferably, the vector is a viral vector. Suitable viral vectors include, for example, retroviral vectors, herpes virus based vectors and parvovirus based vectors (e.g., adeno-associated virus (AAV) based vectors, AAV-adenoviral chimeric vectors, and adenovirus-based vectors). One of ordinary skill in the art has the requisite understanding to determine the appropriate vector for a particular situation.

In a preferred embodiment, the vector is a herpesviral based vector, such as based on HSV. An HSV based viral vector is suitable for use as a vector to introduce a nucleic acid sequence into numerous cell types. The mature HSV virion consists of an enveloped icosahedral capsid with a viral genome consisting of a linear double-stranded DNA molecule that is 152 kb. In a preferred embodiment, the HSV based viral vector is deficient in at least one essential HSV gene. Of course, the vector can alternatively or in addition be deleted for non-essential genes. Preferably, the RSV based viral vector that is deficient in at least one essential HSV gene is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, which are incorporated herein by reference. Preferably, the HSV vector is "multiply deficient," meaning that the HSV vector is deficient in more than one gene function required for viral replication. The sequence of HSV is available on the internet at www.ncbi.nlm.nih.gov: 80/entrez/query.fcgi?cmd=Retrieve&db=nucleotide&list_uids=9629378&d opt=GenBank&term=hsv-1&qty=1, which may facilitate the generation of desired mutations in designing vectors.

The HSV vector can be deficient in replication-essential gene functions of only the early regions of the HSV genome, only the immediate-early regions of the HSV genome, only the late regions of the HSV genome, or both the early and late regions of the HSV genome. The HSV vector also can have essentially the entire HSV genome removed, in which case it is preferred that at least either the viral inverted terminal repeats (ITRs) and one or more promoters or the viral ITRs and a packaging signal are left intact (i.e. an HSV amplicon). The larger the region of the HSV genome that is removed, the larger the piece of exogenous nucleic acid sequence that can be inserted into the genome. However, it is preferred that the vector of the present invention be a non-amplicon HSV vector.

It should be appreciated that the deletion of different regions of the HSV vector can alter the immune response of the mammal. In particular, the deletion of different regions can reduce the inflammatory response generated by the HSV vector. Furthermore, the HSV vector's protein coat can be modified so as to decrease the HSV vector's ability or inability to be recognized by a neutralizing antibody directed against the wild-type protein coat.

The HSV vector, when multiply replication deficient, preferably includes a spacer element to provide viral growth in a complementing cell line similar to that achieved by singly replication deficient HSV vectors. The spacer element can contain any nucleic acid sequence or sequences which are of the desired length. The spacer element sequence can be coding or non-coding and native or non-native with respect to the HSV genome, but does not restore the replication essential function(s) to the deficient region. In addition, the inclusion of a spacer element in any or all of the deficient HSV regions will decrease the capacity of the HSV vector for large inserts. The production of HSV vectors involves using standard molecular biological techniques well known in the art.

Replication deficient HSV vectors are typically produced in complementing cell lines that provide gene functions not present in the replication deficient HSV vectors, but required for viral propagation, at appropriate levels in order to generate high titers of viral vector stock. A preferred cell line complements for at least one and preferably all replication essential gene functions not present in a replication deficient HSV vector. The cell line also can complement non-essential genes that, when missing, reduce growth or replication efficiency (e.g., UL55). The complementing cell line can complement for a deficiency in at least one replication essential gene function encoded by the early regions, immediate-early regions, late regions, viral packaging regions, virus-associated regions, or combinations thereof, including all HSV functions (e.g., to enable propagation of HSV amplicons, which comprise minimal HSV sequences, such as only inverted terminal repeats and the packaging signal or only ITRs and an HSV promoter). The cell line preferably is further characterized in that it contains the complementing genes in a non-overlapping fashion with the HSV vector, which minimizes, and practically eliminates, the possibility of the HSV vector genome recombining with the cellular DNA. Accordingly, the presence of replication competent HSV is minimized, if not avoided in the vector stock, which, therefore, is suitable for certain therapeutic purposes, especially gene therapy purposes. The construction of complementing cell lines involves standard molecular biology and cell culture techniques well known in the art.

When the vector is a replication deficient HSV, the nucleic acid sequence encoding the protein (e.g., GAD protein) is preferably located in the locus of an essential HSV gene, most preferably either the ICP4 or the ICP27 gene locus of the HSV genome. The insertion of a nucleic acid sequence into the HSV genome (e.g., the ICP4 or the ICP27 gene locus of the HSV genome) can be facilitated by known methods, for example, by the introduction of a unique restriction site at a given position of the HSV genome.

A preferred HSV vector for use in the context of the invention contains expanded ICP4, or ICP27 deletions, and preferably both. By "expanded" deletions in this context, it is meant that the preferred vectors have no homologous sequences at either or both of these loci relative to the complementing cell line used for their production. Desirably, the virus has no remaining ICP4 or ICP27 (or both) coding or promoter sequences. Preferably, the deletion in ICP27 extends as well into the UL55 locus, and desirably both genes are deleted. Thus, a most preferred virus for use in the invention contains extended deletions in ICP4, ICP27 and UL 55 such that there is no viral homology to these genes used in a complementing cell line. Desirably, the vector further does not include any homologous DNA sequences to that employed in the complementing cell line (e.g., even using different regulatory sequences and polyadenylation sequences).

As noted above, cell lines complementing the function of genes, particularly essential genes, deleted from an HSV vector are desirable (and in the case of essential HSV genes, necessary) to replicate the vector. Thus, to employ a preferred vector that lacks both ICP4 and ICP27, a cell line engineered to complement both essential genes should be employed. Moreover, as UL55$^-$ HSV strains grow poorly, a cell line complementing it is desirable for use when it is deleted from the vector backbone. Methods for generating complementing cell lines are known to those of ordinary skill in the art.

As noted above, the inventive vector also comprises a nucleic acid sequence encoding a GAD protein (i.e., one or more nucleic acid sequences encoding one or more GAD proteins). The nucleic acid sequence encoding the GAD protein can be obtained from any source, e.g., isolated from nature, synthetically generated, isolated from a genetically engineered organism, and the like. An ordinarily skilled artisan will appreciate that any type of nucleic acid sequence (e.g., DNA, RNA, and cDNA) that can be inserted into a vector can be used in connection with the invention.

The nucleic acid sequence of the inventive vector can encode a secreted protein, e.g., a protein that is naturally secreted by the infected cell. Alternatively, the nucleic acid sequence can encode a protein, such as GAD, that generates a secreted product (e.g., GABA) or peptide by enzymatic catalysis within the cell. Alternatively, the nucleic acid sequence can encode a protein that is not naturally secreted by the cell (i.e., a non-secretable protein), but which comprises a signal peptide that facilitates protein secretion. In this manner, for example, the nucleic acid sequence encodes an endoplasmic reticulum (ER) localization signal peptide and the non-secretable protein. The ER localization signal peptide functions to direct DNA, RNA, and/or a protein to the membrane of the endoplasmic reticulum, wherein a protein is expressed and targeted for secretion. The ER localization signal peptide desirably functions to increase the secretion (i.e., the secretion potential) by a cell of (i) proteins that are not normally secreted (i.e., secretable) by the cell and/or (ii) proteins that are normally secreted by a cell, but in low (i.e., less than desired) quantities. The ER localization signal peptide encoded by the polynucleotide can be any suitable ER localization signal peptide or polypeptide (i.e., protein). For example, the ER localization signal peptide encoded by the nucleic acid sequence can be a peptide or polypeptide (i.e., protein) selected from the group consisting of nerve growth factor (NGF), immunoglobulin (Ig) (e.g., an Ig a chain leader sequence), and midkine (K), or a portion thereof. Suitable ER localization signal peptides also include those described in Ladunga, *Current Opinions in Biotechnology*, 11, 13-18 (2000).

Although the nucleic acid sequence can encode any protein, the protein preferably is a GAD protein or an enkephalin. There are several isoforms of mammalian GAD encoded by several different genes, in particular, GAD25, GAD65, and GAD67. GAD65, targeted principally to membranes and nerve terminals, is regulated by pyridoxal-5'-phosphate and other cofactors. GAD65 is thought to be responsible for the packaging of GABA into vesicles in preparation of synaptic release. Another isoform of mammalian GAD, GAD67, is predominantly cytosolic and its enzymatic activity appears to be regulated by protein level. GAD25 is an alternate splicing variant of GAD67. The vector preferably comprises a nucleic acid sequence coding for GAD67. The coding sequence of the human GAD67 gene and the amino acid sequence of the encoded gene product (i.e., the encoded protein) are publicly available at the National Center for Biotechnology Information (NCBI) website as GenBank Accession No. NM 000817 (SEQ ID NO: 1) and NP_000808 (SEQ ID NO: 2), respectively. Similarly, the coding sequence of the human enkephalin gene and the amino acid sequence of the encoded gene product (i.e., the encoded protein) are publicly available as GenBank Accession No. NM_006211.

The nucleic acid sequence can encode any variant, homolog, or functional portion of the aforementioned proteins. A variant of the protein can include one or more mutations (e.g., point mutations, deletions, insertions, etc.) from a corresponding naturally occurring protein. By "naturally occurring" is meant that the protein can be found in nature and has not been synthetically modified. Thus, where mutations are introduced in the nucleic acid sequence encoding the protein, such mutations desirably will effect a substitution in the encoded protein whereby codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. In addition, a homolog of the protein can be any peptide, polypeptide, or portion thereof, that is more than about 70% identical (preferably more than about 80% identical, more preferably more than about 90% identical, and most preferably more than about 95% identical) to the protein at the amino acid level. The degree of amino acid identity can be determined using any method known in the art, such as the BLAST sequence database. A "functional portion" is any portion of a GAD protein that retains the biological activity of the naturally occurring, full-length GAD protein at measurable levels. A functional portion of the GAD protein produced by expression of the nucleic acid sequence of the vector can be identified using standard molecular biology and cell culture techniques, such as assaying the biological activity of the GAD protein portion in human cells transiently transfected with a nucleic acid sequence encoding the GAD protein portion.

The expression of the nucleic acid sequence encoding the protein is controlled by a suitable expression control sequence operably linked to the nucleic acid sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The nucleic acid sequence encoding the protein in the vector can be regulated by its endogenous promoter or, preferably, by a non-native promoter sequence. Examples of suitable non-native promoters include the human cytomegalovirus (HCMV) promoters, such as the HCMV immediate-early promoter (HCMV IEp), promoters derived from human immunodeficiency virus (HIV), such as the HIV long terminal repeat promoter, the phosphoglycerate kinase (PGK) promoter, Rous sarcoma virus (RSV) promoters, such as the RSV long terminal repeat, mouse mammary tumor virus (MMTV) promoters, the Lap2 promoter, or the herpes thymidine kinase promoter (Wagner et al., *Proc. Natl. Acad. Sci.*, 78, 1444-1445 (1981)), promoters derived from SV40 or Epstein Barr virus, and the like. In a preferred embodiment, the promoter is HCMV IEp. The HCMV IEp promoter can be inserted into the ICP4 locus of the recombinant HSV. Alternatively, expression of the nucleic acid sequence encoding the protein can be controlled by a chimeric promoter sequence. A promoter sequence is "chimeric" if it comprises at least two nucleic acid sequence portions obtained from, derived from, or based upon at least two different sources (e.g., two different regions of an organism's genome, two different organisms, or an organism combined with a synthetic sequence). Techniques for operably linking sequences together are well known in the art.

The promoter can be an inducible promoter, i.e., a promoter that is up- and/or down-regulated in response to an appropriate signal. For example, an expression control sequence up-regulated by a pharmaceutical agent is particularly useful in pain management applications. For example, the promoter can be a pharmaceutically-inducible promoter (e.g., responsive to tetracycline). Examples of such promoters are marketed by Ariad. The promoter can be introduced into the genome of the vector by methods known in the art, for example, by the introduction of a unique restriction site at a given region of the genome. Alternatively, the promoter can be inserted as part of the expression cassette comprising the nucleic acid sequence coding for the protein, such as GAD. In a preferred embodiment, the inducible promoter is operably linked to the polynucleotide sequence encoding for the GAD protein.

Preferably, the nucleic acid sequence encoding the protein further comprises a transcription-terminating region such as a polyadenylation sequence located 3' of the region encoding the protein. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus).

In addition to the nucleic acid encoding the protein (including the promoter and transcription-terminating region), the vector can comprise at least one additional nucleic acid sequence encoding at least one other gene product, e.g., which itself performs a prophylactic or therapeutic function, or augments or enhances a prophylactic or therapeutic potential of the protein. The gene product encoded by the additional nucleic acid sequence can be an RNA, peptide, or polypeptide with a desired activity. If the additional nucleic acid sequence confers a prophylactic or therapeutic benefit, the nucleic acid sequence can exert its effect at the level of RNA or protein. Alternatively, the additional nucleic acid sequence can encode an antisense molecule, a ribozyme, a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation. The additional nucleic acid sequence can encode any one of a variety of gene products that confers a prophylactic or therapeutic benefit, depending on the intended end-use of the composition. The additional nucleic acid sequence also can encode a factor that acts upon a different target than the protein encoded by the nucleic acid sequence of the vector, thereby providing multifactoral treatment. The additional nucleic acid sequence can encode a chimeric protein for combination therapy. The additional gene product can be secreted, or remain within the cell in which it is produced unless or until the cell is lysed. A variety of gene products can enhance the therapeutic potential of the vector.

The additional nucleic acid sequence can encode one gene product or multiple gene products. Alternatively, multiple additional nucleic acid sequences, each encoding one or more gene products, can be inserted into the vector. In either case, expression of the gene product(s) can be separately regulated by individual expression control sequences, or coordinately regulated by one common expression control sequence. Alternatively, expression of the additional nucleic acid(s) can be regulated by the same expression control sequence that regulates expression of the protein encoded by the nucleic acid sequence of the vector; however, any transcription terminating regions present in the nucleic acid encoding the protein would be eliminated to allow for transcriptional readthrough of the additional nucleic acid sequence(s). The additional nucleic acid sequence(s) can comprise any suitable expression control sequence(s) and any suitable transcription-termination region(s) discussed herein in connection with expression of the protein produced by expression of the nucleic acid sequence of the vector.

After the vector has been created, the vector is purified. Vector purification to enhance the concentration of the vector in the composition can be accomplished by any suitable method, such as by density gradient purification, by chromatography techniques, or limiting dilution purification. The vector, preferably a replication deficient HSV vector, is desirably purified from cells infected with the replication deficient HSV vector using a method that comprises lysing cells infected with the HSV vector and collecting a fraction containing the HSV vector.

The cells can be lysed using any suitable method, such as exposure to detergents, freeze-thawing, and cell membrane rupture (e.g., via French press or microfluidization). The cell lysate then optionally can be clarified to remove large pieces of cell debris using any suitable method, such as gentle centrifugation, filtration, or tangential flow filtration (TFF). The clarified cell lysate then optionally can be treated with an enzyme capable of digesting DNA and RNA (a "DNase/RNase") to remove any DNA or RNA in the clarified cell lysate not contained within the vector particles.

Generally, the inventive recombinant HSV is most useful when enough of the virus can be delivered to a cell population to ensure that the cells are confronted with a predefined number of viruses. Thus, the present invention provides a stock, preferably a homogeneous stock, comprising the inventive HSV vector. The preparation and analysis of HSV stocks is well known in the art. For example, a viral stock can be manufactured in roller bottles containing cells transduced with the HSV vector. The viral stock can then be purified on a continuous nycodenze gradient, and aliquotted and stored until needed. Viral stocks vary considerably in titer, depending largely on viral genotype and the protocol and cell lines used to prepare them. Preferably, such a stock has a viral titer of at least about $10^5$ plaque-forming units (pfu), such as at least about $10^6$ pfu or even more preferably at least about $10^7$ pfu. In still more preferred embodiments, the titer can be at least about $10^8$ pfu, or at least about $10^9$ pfu, and high titer stocks of at least about $10^{10}$ pfu or at least about $10^{11}$ pfu are most preferred.

The invention additionally provides a composition comprising the HSV vector and a carrier, preferably a physiologically-acceptable carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease.

Antibiotics, i.e., microbicides and fungicides, can be present to reduce the risk of infection associated with gene transfer procedures and other disorders.

The invention also provides a method of treating spinal cord injury pain or peripheral neuropathic pain in a mammal comprising administering to a mammal a vector or composition of the present invention comprising a nucleotide sequence encoding a glutamic acid decarboxylase (GAD) protein in an amount effective to treat spinal cord injury pain or peripheral neuropathic pain. In a preferred embodiment, the administered vector is a viral vector. In a preferred embodiment, the mammal is a human.

The method of treating spinal cord injury pain or peripheral neuropathic pain further can comprise the administration (i.e., pre-administration, co-administration, and/or post-administration) of other treatments and/or agents to modify (e.g., enhance) the effectiveness of the method. The method of the invention can further comprise the administration of other substances which locally or systemically alter (i.e., diminish or enhance) the effect of the composition on a host. For example, substances that diminish any systemic effect of the protein produced through expression of the nucleic acid sequence of the vector in a host can be used to control the level of systemic toxicity in the host. Likewise, substances that enhance the local effect of the protein produced through expression of the nucleic acid sequence of the vector in a host can be used to reduce the level of the protein required to produce a prophylactic or therapeutic effect in the host. Such substances include antagonists, for example, soluble receptors or antibodies directed against the protein produced through expression of the nucleic acid sequence of the vector, and agonists of the protein.

One skilled in the art will appreciate that suitable methods of administering the inventive vector and composition of the invention to an animal (especially a human) for therapeutic or prophylactic purposes, e.g., gene therapy, vaccination, and the like (see, for example, Rosenfeld et al., *Science*, 252, 431-434 (1991), Jaffe et al., *Clin. Res.*, 39(2), 302A (1991), Rosenfeld et al., *Clin. Res.*, 39(2), 311A (1991), Berkner, *BioTechniques*, 6, 616-629 (1988)), are available, and, although more than one route can be used to administer the composition, a particular route can provide a more immediate and more effective reaction than another route. A preferred route of administration involves transduction of DRG neurons through peripheral inoculation to release GABA in the dorsal horn. In many embodiments, this can be accomplished by delivering the GAD vector by subcutaneous inoculation, which is an attractive feature of the inventive approach to treat SCI pain or peripheral neuropathic pain.

The dose administered to an animal, particularly a human, in the context of the invention will vary with the particular vector, the composition containing the vector and the carrier therefor (as discussed above), the method of administration, and the particular site and organism being treated. The dose should be sufficient to effect a desirable response, e.g., therapeutic or prophylactic response, within a desirable time frame. Thus, the dose of the vector of the inventive composition typically will be about $1\times10^5$ or more particle units (e.g., about $1\times10^6$ or more particle units, about $1\times10^7$ or more particle units, $1\times10^8$ or more particle units, $1\times10^9$ or more particle units, $1\times10^{10}$ or more particle units, $1\times10^{11}$ or more particle units, or about $1\times10^{12}$ or more particle units). The dose of the vector typically will not be $1\times10^{13}$ or less particle units (e.g., $4\times10^{12}$ or less particle units, $1\times10^{12}$ or less particle units, $1\times10^{11}$ or less particle units, or even $1\times10^{10}$ or less particle units).

The following examples further illustrate the invention but, of course, should not be construed as in any way limiting its scope. In these examples, several measurements were recorded and statistically analyzed. The statistical significance of the difference between vector treated and control animals was determined using multivariate analysis of variance or the Kruskal-Wallis test for non-parametric measures.

Single comparison was performed with Student's t test, using a P value of <0.05 as significant. All data are expressed as means±the standard error of the mean (SEM).

EXAMPLE 1

This example demonstrates the construction of the GAD vector.

The nonreplicating HSV vector QHGAD67 is defective in expression of the HSV immediate early (IE) genes ICP4, ICP22, ICP27, and ICP47, and contains the human GAD67 gene under the control of the human cytomegalovirus immediate early promoter (HCMV IEp) in the UL41 locus (FIG. 1). Control vector Q0ZHG (constructed according to the method described in Chen et al. *J. Virol*, 74(21), 10132-41 (2000)) is defective in the same genes, but contains the *Escherichia coli* lacZ reporter gene in the same position (FIG. 1).

GAD67 cDNA (constructed according to the method described in Bu, D. F., et al., *Proc. Natl. Acad. Sci. USA*, 89, 2115-2119 (1992)) was individually sub-cloned as a ClaI/XbaI fragment downstream of the human cytomegalovirus immediate early promoter in the shuttle plasmid p41H, containing the promoter and adequate HSV flanking DNA sequence in order to enable efficient homologous recombination at the $U_L41$ gene locus of the vector. The expression/targeting cassette was recombined into the $U_L41$ locus of vector Q0ZHG by cotransfection of complementing 7b cells with PmeI-digested viral and targeting plasmid DNA to replace the LacZ marker gene with the GAD expression construct. The recombinant QHGAD67 was purified by three rounds of limiting dilution purification and the genetic structure confirmed by Southern blot. Vector stocks were produced in 7b cells in roller bottles, purified on a continuous nycodenze gradient, and aliquotted and stored at −80° C. until thawed for use. The titer of the final vector product was determined as described in Krisky, D., et al., *In Methods in Molecular Medicine*, Human Press, Totowa, N.J. (1996))

EXAMPLE 2

This example demonstrates the construction of an HSV vector having extended deletions of the ICP4 and ICP27 loci and a deletion of UL55.

Figure 14:
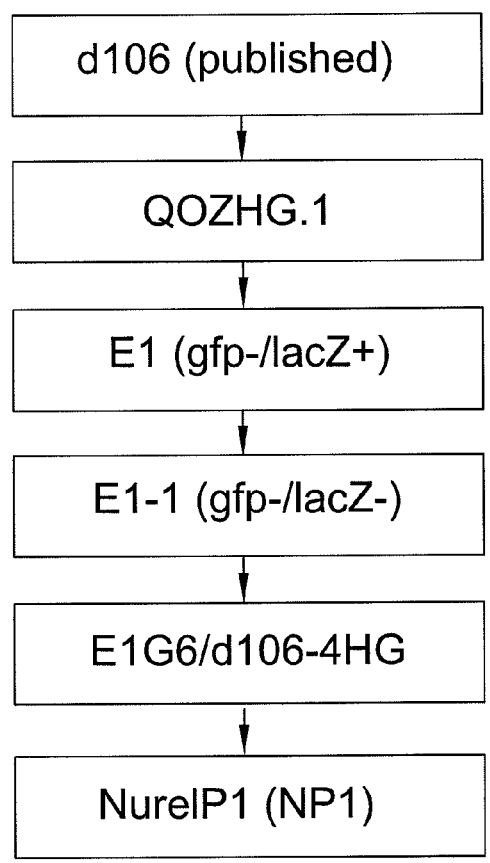
FIG. 14 depicts the construction of an HSV vector having extended deletions of the ICP4 and ICP27 loci and a deletion of UL55.
Figure 14:
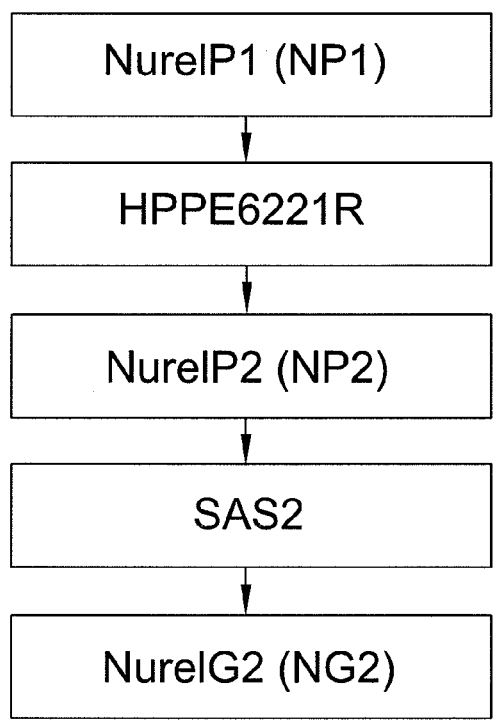

The schematic for constructing this vector is set forth in FIG. 14. Specifically, plasmid d106 (Hadjipanayis and DeLuca, Can Res 65(12): 5310-6 (2005)) was virally crossed with plasmid TOZ.1 (Arafat et al., Clin Can Res 6: 4442-8 (2000)) to produce QOZHG.1. The details of vector QOZHG.1 are described in Example 1 and its construction described in Chen et al., J Virol 74(21), 10132-41 (2000).

Plasmid pPXE (Niranjan et al., Mol Ther 8(4).530-42 (2003)) was recombined into the ICP27 locus of QOZHG.1 to rescue the previous ICP27 deletion and to remove HCMV-eGFP gene. A single recombinant was then isolated, purified and verified by selecting a plaque that did not exhibit green fluorescence under a fluorescent microscope. The recombinant was termed E1. E1 was negative for the GFP gene and positive for the LacZ gene.

Plasmid 41HN was produced by cloning the Hind III to Not I fragment (HSV-1 genomic nucleotides 90145 to 93858) containing the UL41 coding sequence into the Hind III to Not I sites of pBSSK (Stratagene). Plasmid 41HN was then recombined into the UL41 locus of E1 to rescue the wildtype UL41 gene and remove LacZ. The resulting vector, named E1-1 was isolated, purified, and verified by standard methods. This vector was negative for both gfp and lacz genes.

Plasmid pSASB3 was constructed by cloning the Sph I to Afl III (Sal I Tinkered) fragment (1928 bp) of the HSV-1 KOS strain genome (nucleotides 124485-126413) into Sph I/Sal I digested pSP72 followed by insertion of a the 695 bp BglII to BamH I fragment (nucleotides 131931 to 132626) containing regions upstream of the ICP4 promoter including the viral origin contained within the short inverted repeat regions into the Bgl II to BamH I sites of the vector plasmid.

Plasmid pSASB3gfp was contructed by cloning a HCMV-eGFP fragment in the BamHI site of pSASB3. Plasmid pSASB3gfp was then recombined into the ICP4 locus of E1-1 to expand the ICP4 deletion. The resulting vector, named E1G6/d106-4HG was then isolated, purified, and verified by standard methods.

The plasmid pSASB3-HPPE was created by cloning a EcoR I to Sal I fragment of the plasmid pCMV-hPPE from Dr. Steven Wilson, University of South Carolina (Liu F, Housley P R, Wilson S P. [J. Neurochem. 1996 October; 67(4):1457-62) containing the HCMV immediate early promoter, SV40 intron (180 bp XhoI-PstI) from the 16s/19s RNA of SV40, the entire hPPE coding sequence, and the SV40 polyadenylation signal (SV40 bases 2533 to 2729 into plasmid pSASB3 at the unique Sal I site. Sal I release of the hPPE expression construct was made possible by previous EcoR I digestion followed by Klenow fragment blunting of the EcoR I site and ligation with a Sal I linker. The product of this ligation was then digested with Sal I to purify the Sal I flanked expression construct. pCMV-HPPE was subcloned from a cDNA clone pUR292 from Dr. Barbara Spruce as 946 bp BamHI-HindIII fragment from pUR292 that was blunt-ended, NotI linkers added, and cloned into the unique NotI site of the expression plasmid pCMVβ.

The final enkephalin expression/ICP4 targeting construct (pSASB3-HPPE) contains the following elements; 1) bases 131931 to 132626 of the HSV genome to provide a 5' recombination flanking sequence targeting the ICP4 locus, 2) the human cytomegalovirus (HCMV) immediate early promoter (IEp), 3) the SV40 16s/19s intron splice donor and acceptor sites, 4) the preproenkephalin cDNA, 5) the SV40 late polyadenylation signal, 6) bases 124485 to 126413 of the HSV genome to provide a 3' recombination flank targeting the ICP4 locus.

Plasmid pSASB3-hppe was then recombined into the ICP4 locus of E1G6/d106-4HG to produce the NureIP1 (NPP1) vector, which is generically known as 6221.

Plasmid PS-UB6R-6 was created by cloning a Bgl II-BamH I flanked ubiquitin promoter driven Red2 (Invitrogen) in the BamH I site of PSP4. The BamH I site of PSP.4 is located in between the 5' ICP27 flank fragment and the UL56 coding sequence.

Plasmid PS-UB6R-6 was recombined into the ICP27 locus of NP1 to expand the ICP27 deletion to include all of ICP27 and UL55 and to insert the UB6-Red gene. The resulting vector, termed HPPE6221R, was isolated, purified, and verified by selecting red plaques.

Plasmid PSP4 was created by cloning the EcoR I to BamH I (HSV-1 genomic 110095 to 113322) sequence 5' to the ICP27 coding sequence into the plasmid PS.2. PS.2 contains the Dde I to Sma I (HSV-1 genomic fragment 116156 to 117119) blunt end ligated into the Not I site of pBSSK (Stratagene).

Plasmid PSP4 was recombined into the ICP27 locus of HPPE6221R vector to remove UB6-Red and to leave the ICP27/UL55 deletion. The resulting vector, termed NureIP2 (NP2), was isolated, purified, and verified by standard methods.

Plasmid pSASB3GFP was recombined into the ICP4 locus of NP2 to replace HCMV-hppe with HCMV-eGFP. The resulting vector, termed SAS2, was then isolated, purified, and verified by standard methods.

Plasmid pRC2 (Invitrogen) was modified sequentially by converting the 1) HinDIII site into a ClaI site, 2) the BbvII site into a HinDIII site, 3) the resulting HinDIII site into a BglII site to make plasmid pRC2HB2. The BglII fragment of pRC2HB2, about 1200 base pairs, was cloned into the BamHI site of plasmid pSASB3 creating plasmid pSHB3. Separately the GAD67 clone was modified by converting the HinDIII site into a BamHI site creating pGADHB2. The resulting 2.8 kb BamHI fragment from pGADHB2 was cloned into the BamHI site of pSHB3 to make pGADL1.

Plasmid pGAD-L1 was recombined into the ICP4 locus of SAS2 to produce the vector NurelG2 (NG2).

The vectors NP2, SAS2 and NG2 are vectors that have no homology with the cell line, such that no homologous recombination can take place between the cell line and the vector. Therefore, these vectors are ideal for using in combination with the ICP4, ICP27, UL55 complementing cell line for vector production.

EXAMPLE 3

This example demonstrates the expression of GAD protein by GAD vector transduced cells.

Figure 2:
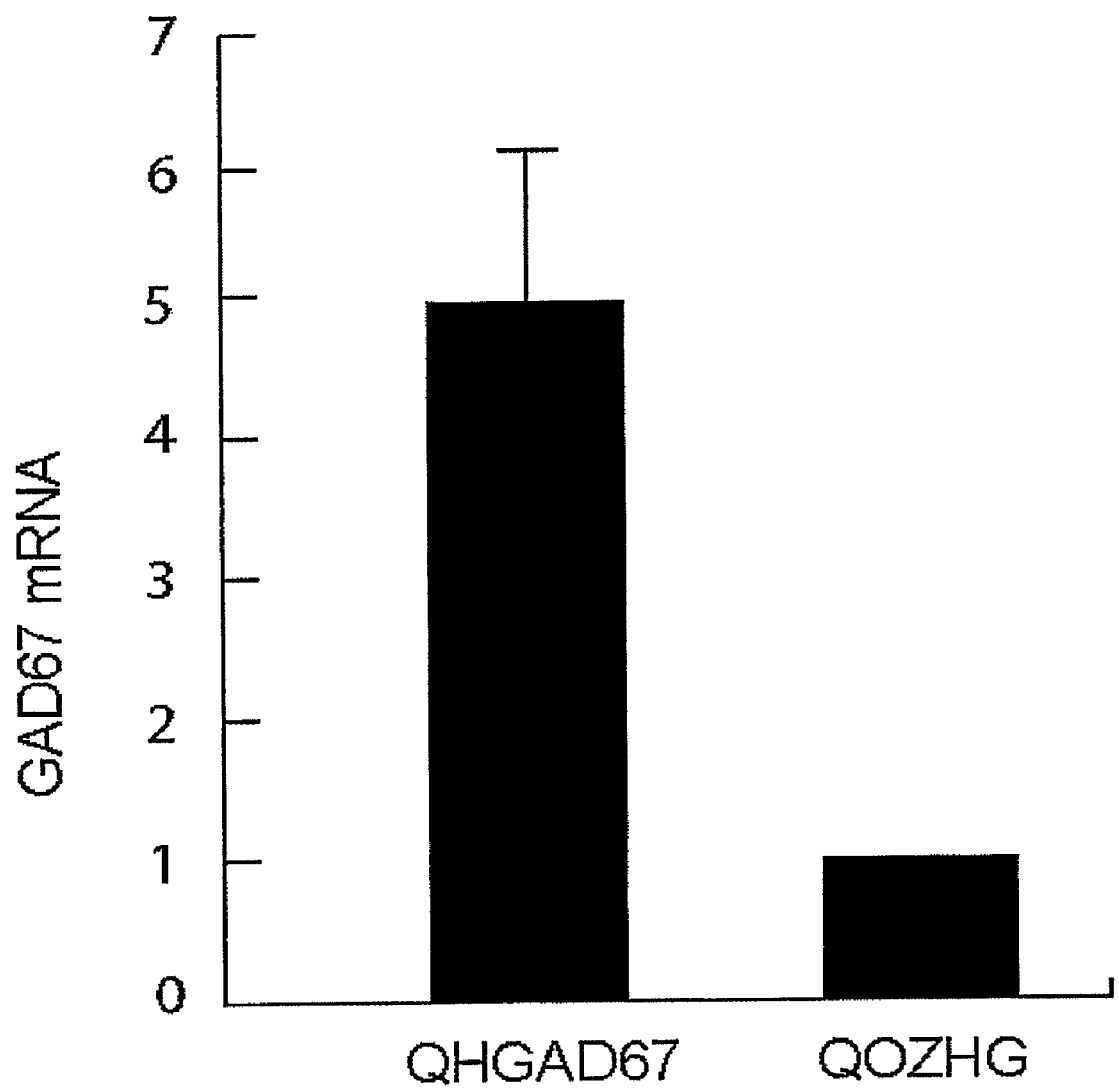
FIG. 2 is a representation of QHGAD67 transduction by footpad inoculation increased GAD67 mRNA in lumbar dorsal root ganglia (DRG). One week after subcutaneous inoculation of 30 μl of $1\times10^9$ pfu/ml QHGAD67 or Q0ZHG into one hind paw total RNA was extracted from the pooled L4-L6 DRG (500 ng), amplified by real-time PCR, and quantitated using GAPDH as a standard. The amount relative to Q0ZHG-transduced ganglia is represented. Means ±Standard Error Mean (SEM), N=6.

One week after subcutaneous inoculation of QHGAD67 into the plantar surface of the hind paw of a laboratory rat the amount of GAD67 mRNA in the pooled L4-L6 DRG detected by real-time RT-PCR was fivefold greater than in contralateral DRG transduced with Q0ZHG (FIG. 2). Also, GAD67 immunoreactivity in transduced DRG was present in neurons in a broad spectrum of DRG neurons of all sizes compared to the contralateral (vehicle-injected) DRG. GAD67 protein, determined by Western blot, was significantly increased in both the lumbar DRG (0.048±0.009 OD units) compared to sham-inoculated controls (0.025±0.006 OD units, P<0.01.

Figure 3:
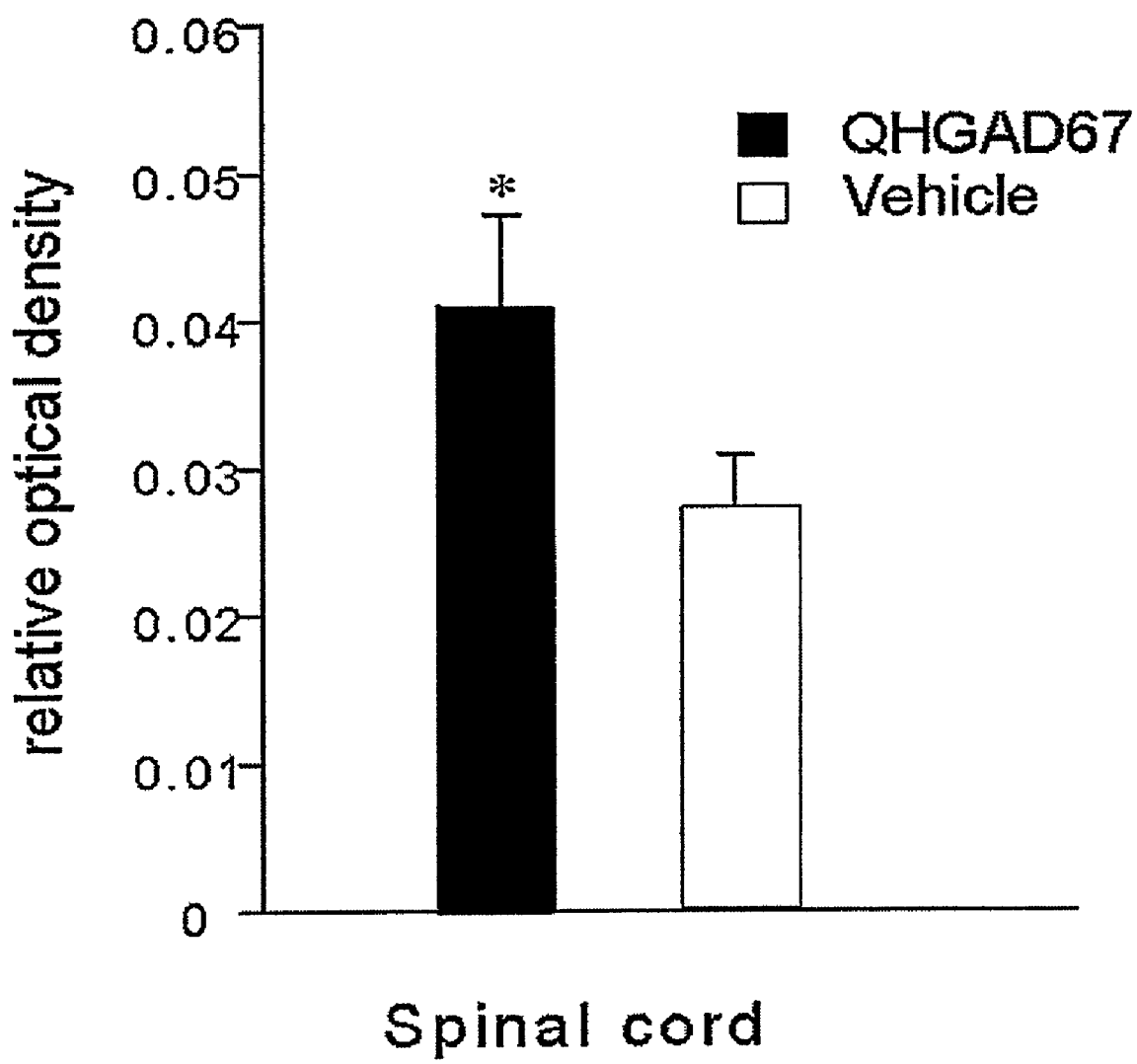
FIG. 3 represents protein from the dorsal quadrant of lumbar spinal cord determined by Western blot using β-actin as an internal standard and quantitated by relative optical density. Means±SEM, N=6, *$P<0.05$. increased GAD67-like immunoreactivity after transduction with QHGAD67.

One week after subcutaneous inoculation of 30 µl of $11 \times 10^9$ pfu/ml QHGAD67 increased immunoreactivity was seen predominantly in laminae II and III compared to the contralateral (vehicle-injected) dorsal horn. In the superficial dorsal horn of control rats GAD67 immunoreactivity was located predominantly in small round cells of lamina III with few neuritic extensions that appeared to be endogenous GABA-ergic interneurons in the superficial dorsal horn and some smaller, punctuate, densely staining, irregular profiles that appeared to be varicosities or small axonal terminals. The intensity of immunostaining was increased substantially in the dorsal horn containing central terminals of the axons from DRG transduced with QHGAD67 and the increased immunoreactivity appeared to be located in the irregular profiles representing axonal terminals. By Western blot the amount of GAD in the dorsal spinal cord of the lumbar segments containing the central terminal of those axons (0.041±0.008 OD units) was significantly increased compared to the sham-inoculated controls (0.027±0.004 OD units) (P<0.01, FIG. 3).

The analysis of GAD RNA by real-time RT-PCR was performed as follows: L4-6 DRGs were rapidly removed and total RNA extracted from the pooled L4-6 ganglia using TriReagent (Sigma). After DNase I digestion, first-strand cDNA was produced using Omniscript reverse transcriptase (Qiagen, Valencia, Calif., USA). Primers and probes for GAD67 and GAPDH (Synthegen, Houston, Tex., USA) were designed using Primer Express (Applied Biosystems, Foster City, Calif., USA). GAD67 forward primer SEQ ID NO: 3; reverse primer SEQ ID NO: 4; probe, SEQ ID NO: 5 (Synthegen); and GAPDH forward primer SEQ ID NO: 6; reverse primer SEQ ID NO: 7; probe SEQ ID NO: 8 (Invitrogen). PCRs were performed in an ABI Prism 7700 sequence detection system (Applied Biosystems) in a total volume of 50 µl. The amount of RNA was determined using GAPDH as an internal control and calculated relative to DRG transduced with Q0ZHG. Each PCR amplification was performed in triplicate wells, using the following conditions: 2 minutes at 50° C. and 10 minutes at 95° C., followed by 40 cycles of 15 s at 95° C. and 1 minute at 60° C.

The amount of GAD67 protein was determined by Western blot according to the following protocol. The L4-L6 DRG or the dorsal quadrant of the lumbar enlargement (L4 to L6 segments) of spinal cord was sonicated in homogenization buffer (100 mg tissue/ml) consisting of 60 mM phosphate buffer, pH 7.4, 1 mM phenylmethylsulfonyl fluoride and 0.5% TritonX-100. The homogenate was centrifuged for 15 minutes at 100,000 g, using a TL100 ultracentrifuge (Beckman), and the total protein in the supernatant was measured by Bradford assay (BioRad, Hercules, Calif., USA). Proteins were separated on a 4-15% SDS gradient polyacrylamide gel, transferred to nitrocellulose membrane (Immobilon-P, Millipore, Billerica, Mass., USA), incubated with rabbit anti-GAD67 (1:4000, Chemicon, Temecula, Calif., USA) followed by horseradish peroxidase-conjugated goat anti-mouse (1:10,000, Jackson Laboratories, Bar Harbor, Me., USA), and detected by enhanced chemiluminescence (NEN, Boston, Mass., USA). The membranes were stripped and reprobed with rabbit anti-β-actin as a loading control. The intensity of each band was determined by quantitative densitometry using a PC-based image analysis system (MCID, Imaging Research, Brock, Ontario, Canada).

EXAMPLE 4

This example demonstrates the increased release of GABA in GAD vector transduced cells.

Primary DRG neurons transduced in vitro with QHGAD67 at a multiplicity of infection (m.o.i.) of 1 released GABA into the medium (9.53±2.15 pmol/10 µl) in amounts substantially greater than those released from control (2.34±0.22 pmmol/10 µl, P<0.01) or Q0ZHG-transduced DRG neurons (2.56±0.54 µmol/10 µl, P<0.01) (FIG. 4A). The in vivo amount of GABA released into the dorsal spinal cord from the central terminals of DRG transduced by subcutaneous inoculation into the foot 1 week earlier was determined by microdialysis from a catheter implanted in the ipsilateral lumbar dorsal horn. GABA contained in the dialysate collected from animals inoculated with Q0ZHG contained 0.74±0.24 pmol/10 µl compared to the dialysate from animals inoculated with QHGAD67 which contained 1.46±0.25 pmol/10 µl (P<0.05) (FIG. 4B).

Dissociated DRG neurons from 17-day-old rat embryos were plated on poly-D-lysine-treated coverslips at a density of $10^5$ cells/well in a 24-well plate. Each well contained 500 µl Neurobasal medium containing B27, Glutamax I, Albumax II, and penicillin/streptomycin (Gibco-BRL, Carlsbad, Calif.), supplemented with 100 ng/ml of 7.0S NGF (Sigma, St. Louis, Mo.). At 14 days in culture, the cells were infected with either QHGAD67 or Q0ZHG at a m.o.i. of 1 for 1 hour, after which the virus was removed. Forty-eight hours later the medium was changed to 100 µl of artificial cerebrospinal fluid and after 5 minutes collection time the bathing solution was centrifuged 5 minutes at 10,000 g and the supernatant taken for determination of GABA by HPLC. The DRG cells were examined for expression of GAD67 protein by immunocytochemistry.

The amount of GABA released from nerve terminals in the dorsal horn in vivo was determined by HPLC of a microdialysate using the following protocol: Rats were anesthetized with chloral hydrate (400 mg/kg), the laminae of T11 and T12 vertebrae that overlie the lumbar segments of the spinal cord were removed, leaving the dura intact, and the animals were fixed in a stereotaxic apparatus. A heating lamp was used to prevent heat loss and the body temperature was kept at 37.5° C. using a feedback sensor. A small dural incision lateral to midline was made with a sharp needle, and a microdialysis probe (CMA/11, cuprophane dialysis membrane, length 1 mm, diameter 0.24 mm, molecular cut-off 6 kDa, CMA/Microdialysis, Stockholm, Sweden) was inserted into the dorsal horn through the dural incision and perfused with artificial cerebrospinal fluid (CMA/Microdialysis) at a rate of 1 µl/min. After 1 h to allow for equilibration with the extracellular fluid, samples were collected for 1 h. At the end of the experiment, the probe was checked for the presence of air bubbles and the position in the dorsal horn of the spinal cord verified by microscopy of perfusion-fixed sections.

Next, the amount of GABA released from transduced cells in vitro, or collected by microdialysis in vivo, was determined using HPLC with 6-aminoquinolyl-N-hydroxysuccinimidyl carbamate derivatization (AccQ.Fluor Reagent Kit; Waters, USA). Twenty microliters of culture solution was mixed with 20 µl of derivatizing reagent in 60 µl of borate buffer; 10 µl of the sample was allowed to react for 10 minutes at 55° C. and separated by gradient HPLC (Waters 2695 Separations Module) on an AccQ.Taq column (3.9×150 mm; Waters) with a mobile phase consisting of Fluent A (Waters) and acetonitrile and a flow rate of 1 ml/min. The peaks were detected by fluorescence at 37° C. (Waters 2475 Detector) using an excitation wavelength of 250 nm and emission wavelength of 395 nm.

The intrathecal catheter was surgically implanted in the laboratory rat according to the following protocol: An intrathecal catheter was placed 1 week after T13 left spinal hemisection using a modification of the method of Storkson. Briefly, the animals were reanesthetized with chloral hydrate (400 mg/kg), a longitudinal incision was made from L2 to L6 a few millimeters left of the midline, and a polyethylene catheter (PE-10, Clay Adams, Parsippany, N.J., USA) was introduced from the L4-L5 intervertebral space into the lumbar subarachnoid space so that the tip of the catheter was located near the lumbar enlargement of the spinal cord. The distal end of the catheter was tunneled subcutaneously to emerge at the neck, leaving 7 µl of dead space. After implantation of the intrathecal catheter, the rats were housed in individual cages and those animals showing evidence of motor dysfunction were sacrificed. The location of the catheter tip was confirmed by infusion of 15 µl of lidocaine (20 mg/ml) followed by 8 µl of saline to produce a motor paralysis lasting for 20-30 minutes. Intrathecal drug administration was performed using a microinjection syringe (Hamilton Co., Reno, Nev., USA) connected to the intrathecal catheter in awake, briefly restrained rats.

EXAMPLE 5

This example demonstrates that subcutaneous inoculation of a GAD vector in a laboratory rat reduces mechanical allodynia and thermal hyperalgesia after SCI.

Figure 5:
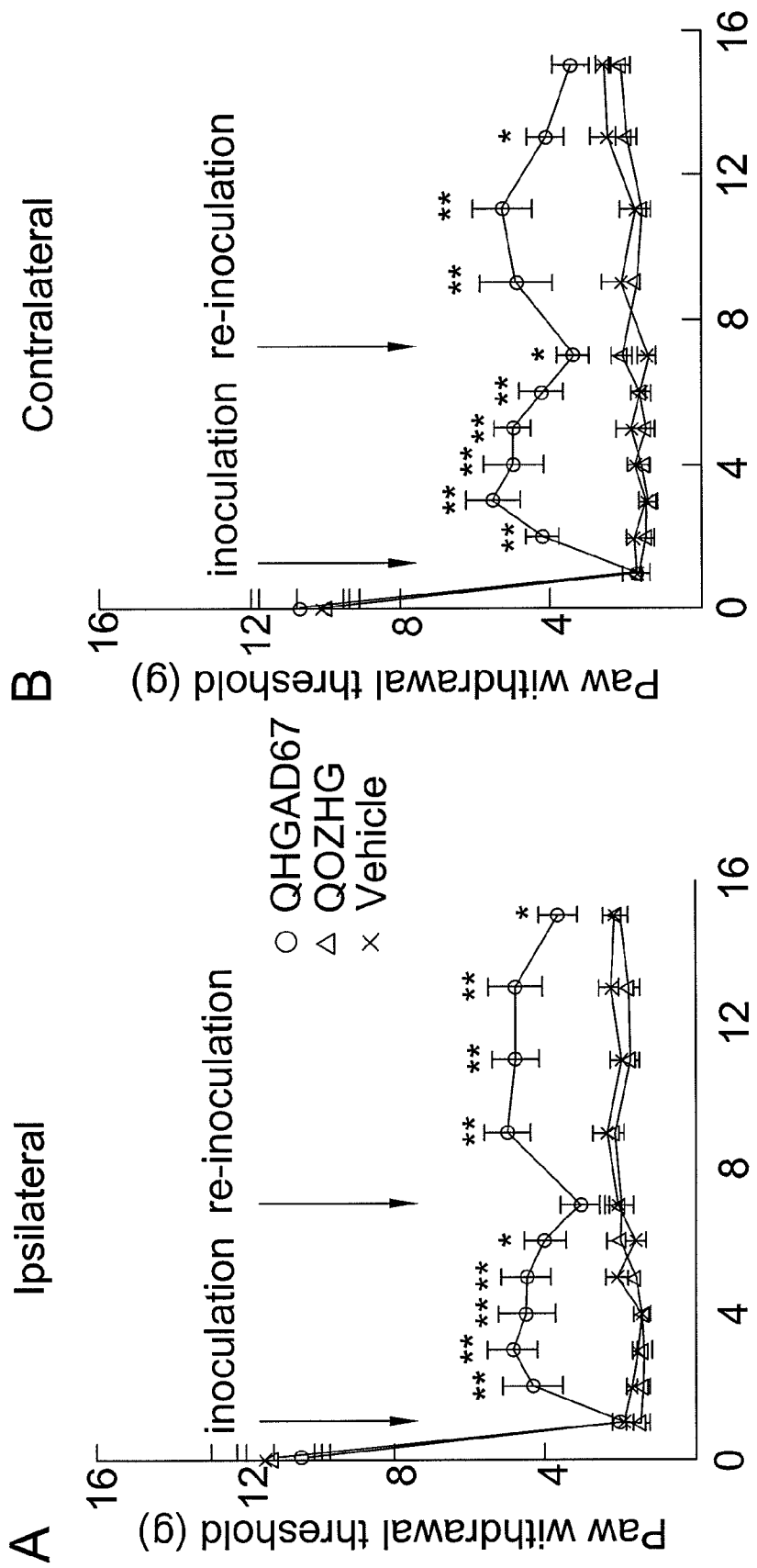
FIGS. 5A-D are representations of the mechanical allodynia and thermal hyperalgesia were significantly reduced by QHGAD67 inoculation.
Figure 5:
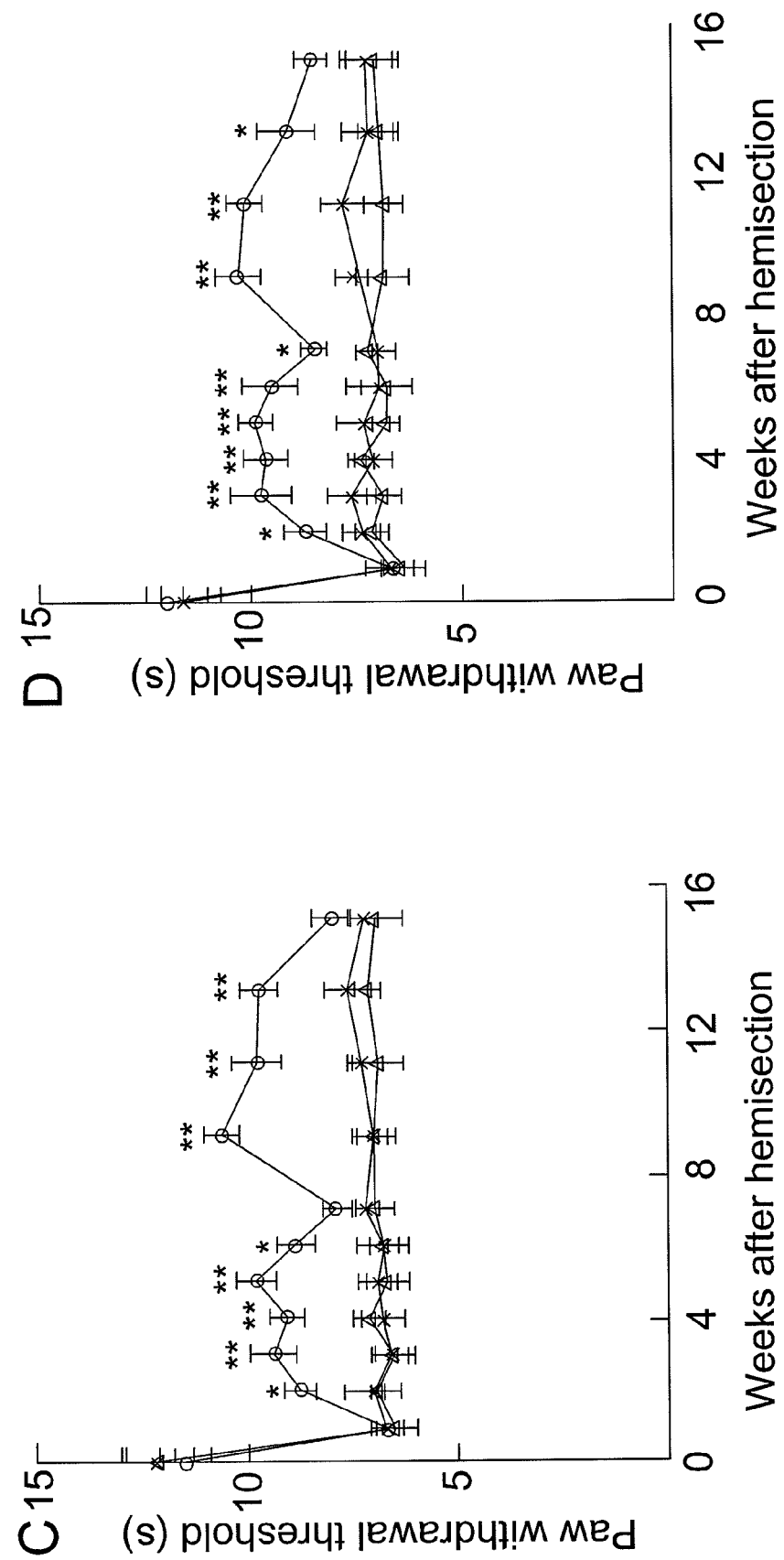

One day after T13 left spinal cord hemisection, all animals showed ipsilateral hind-limb paralysis with no motor dysfunction in the hind limb contralateral to spinal cord hemisection. Two weeks after spinal cord hemisection, there was considerable return of motor function (BBB score of 12-13, data not shown). A BBB score of 12, corresponding to frequent-to-consistent weight-supporting phantom steps and occasional front leg-hind leg coordination is sufficient to allow full behavioral testing of somatosensory-induced paw withdrawal. At one week after spinal cord hemisection, mechanical allodynia, manifested by a significant decrease in hind-paw withdrawal threshold to a graded series of von Frey filament stimuli (1.71±0.35 g ipsilateral, 1.9±0.52 g contralateral) as compared to the preoperative threshold (11.2±1.68 g ipsilateral, 11.6±1.71 g contralateral), in both hind paws was observed. Inoculation of QHGAD67 ($1 \times 10^9$ pfu/ml, 30 µl/paw) subcutaneously in the plantar surface of the hind paws bilaterally one week after spinal cord hemisection significantly increased the hind-paw withdrawal threshold (4.4±1.12 g ipsilateral, 4.1±0.75 g contralateral) measured one week after inoculation (two weeks after injury). Control animals inoculated with Q0ZHG showed no change in their mechanical threshold (1.8±0.28 g ipsilateral, 1.6±0.34 g contralateral, P<0.01 compared to QHGAD67). The maximal antiallodynic effect (i.e., increase in paw withdrawal threshold) occurred two weeks after QHGAD67 inoculation (5.19±0.82 g ipsilateral and 5.8±1.14 g contralateral) and the antiallodynic effect persisted for five weeks, decreasing to 2.86±0.63 g ipsilateral and 3.2±0.47 g contralateral at six weeks after inoculation (FIGS. 5A and 5B). Reinoculation with the same dose of QHGAD67 into the footpads bilaterally at six weeks after initial inoculation reestablished the antiallodynic effect. The magnitude of the effect obtained by reinoculation was at least as great as that produced by the initial injection of the vector, and the duration of the effect produced by reinoculation was slightly longer (6-7 weeks) than that which resulted from the initial inoculation. There was no significant difference in paw withdrawal thresholds between Q0ZHG-inoculated and vehicle-treated rats at all time points (FIGS. 5A and 5B).

After spinal cord hemisection, animals also demonstrated thermal hyperalgesia manifested by a decrease in withdrawal latency in response to noxious thermal stimuli (6.7±0.51 s ipsilateral, 6.9±0.6 s contralateral) compared to the preoperative values (12.6±1.23 s ipsilateral, 12.1±1.25 s contralateral). One week after inoculation of QHGAD67 (two weeks after spinal cord hemisection) there was a statistically significant increase in thermal latency (8.8±0.48 s ipsilateral, 8.7±0.71 s contralateral) compared to Q0ZHG-inoculated controls (6.5±0.43 s ipsilateral, 7.1±0.42 sec contralateral). The time courses of antihyperalgesic effect were similar to those of antiallodynic effect of the vector (FIGS. 5C and 5D), except that the peak effect occurred four weeks after inoculation (9.7±0.71 s ipsilateral, 9.62±0.78 s contralateral). Reinoculation of QHGAD67 vector at six weeks also reestablished the antihyperalgesic effect. The duration and the magnitude of the antihyperalgesic effect after the second inoculation was longer and greater than those which followed the initial inoculation. There was no significant difference between vehicle-treated and Q0ZHG-inoculated animals in both hind-paw withdrawal latencies at any time period (FIGS. 5C and 5D).

For these tests, male Sprague-Dawley rats, weighing 175-200 g were used. Housing conditions and experimental procedures were approved by the University of Pittsburgh Institutional Animal Care and Use Committee. With the rat under chloral hydrate anesthesia (400 mg/kg) the T11-T12 spinal laminae were located by palpating the last rib (attached to T13). A longitudinal incision was made exposing several segments, and a laminectomy was performed at two vertebral segments (T11-T 12). The lumbar enlargement was identified by accompanying dorsal vessels, and the spinal cord was hemisected at T13 using a No. 11 scalpel blade with care taken not to damage the major dorsal vessels and vascular branches. A tuberculin syringe with a 28-gauge needle was placed dorsoventrally at the midline of the cord and pulled laterally to ensure that the spinal cord hemisection was complete. Muscle and fascia were sutured closed, and the skin was closed with autoclips. Following surgery, animals were maintained under the same preoperative conditions. All the animals were eating and drinking within 3 hours after surgery. Locomotor function was observed and recorded using the BBB Locomotor Rating Scale to ensure that motor recovery of the limb ipsilateral to the spinal cord hemisection was sufficient to allow for somatosensory behavioral testing. Animals that demonstrated a loss of locomotion in both hind limbs, indicating bilateral corticospinal tract transaction, were excluded from the study at that time. Animals that met the criteria were then inoculated with a vector. Six animals in each group were inoculated with a vector and tested by reinoculation.

Behavioral testing for mechanical allodynia and thermal hyperalgesia was performed during the day portion of the circadian cycle (8:00 AM to 5:00 PM). Mechanical allodynia was assessed by measuring the threshold of paw-withdrawal response to graded mechanical stimuli using a series of von Frey filaments (0.4, 0.7, 1.2, 1.5, 2.0, 3.6, 5.5, 8.5, 11.8, and 15.1 g). Rats were placed in transparent plastic cubicles on a mesh floor for a period of at least 30 minutes for acclimatization, after which von Frey filaments were applied to the plantar surface of the foot serially in ascending order of strength with sufficient force to cause slight bending against the paw and held for 6 s. A brisk foot withdrawal to von Frey filament application was regarded as a positive response and cause to present the next weaker stimulus. Thermal hyperalgesia was assessed by measuring the latency of paw withdrawal from a radiant heat source. In this test, the rats were placed on a glass plate over a light box. After a ten minute habituation period the plantar surface of the paw was exposed to a beam of radiant heat applied through the glass floor. The light beam was turned off automatically by a photocell when the rat lifted the limb, allowing the measurement of time between the start of the light beam and the paw withdrawal. This time was defined as the paw withdrawal time. Testing was always performed in triplicate at five minute intervals and twenty seconds was used as the cut-off time.

EXAMPLE 6

This example demonstrates that the behavioral effects of GAD vector inoculation are reversed by bicuculline and phaclofen.

Figure 6:
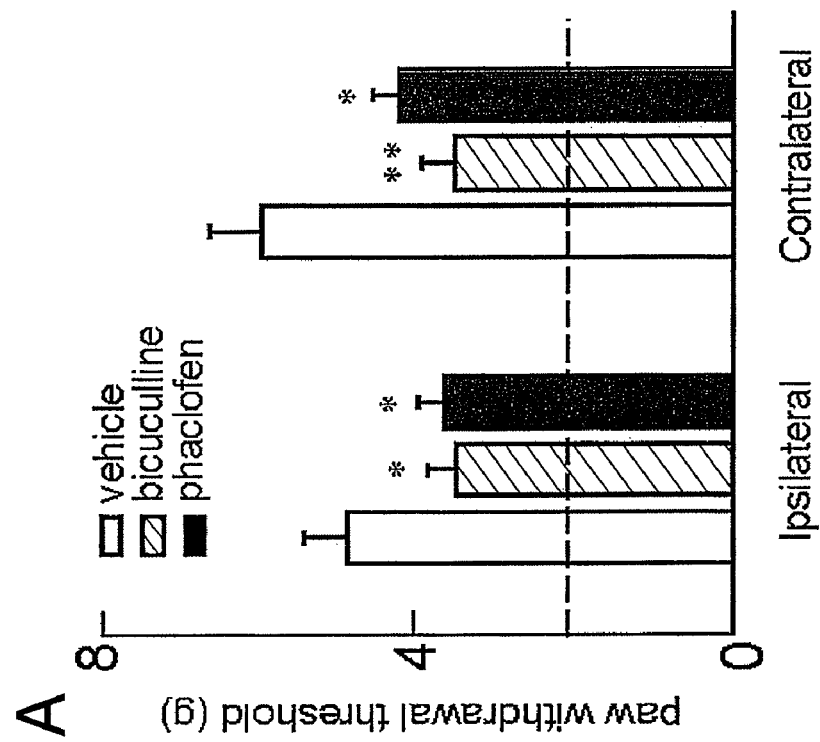
FIGS. 6A and 6B demonstrate that bicuculline (0.5 μg) or phaclofen (0.8 μg) administrated intrathecally 3 weeks after hemisection and 2 weeks after footpad inoculation partially reversed the (A) antialiodynic and (B) antihyperalgesic effects of vector inoculation. The dotted line represents the mean threshold (A) and latency (B) in animals after SCI inoculated with control vector or vehicle. Means±SEM, N=6, *$P<0.05$, **$P<0.01$ vs vehicle-treated.

The pharmacologic basis of the QHGAD67-mediated antinociceptive effect using the $GABA_A$ receptor-selective antagonist bicuculline and the $GABA_B$ receptor-selective antagonist phaclofen was examined. Intrathecal administration of bicuculline (0.5 μg; Sigma) or phaclofen (0.8 μg; Sigma) to sham-operated animals two weeks after surgery did not alter the mechanical threshold or thermal latency. Administration of the same dose of bicuculline to rats with spinal cord hemisection inoculated with QHGAD67 reduced the mechanical threshold from 4.87±1.13 g to 3.5±0.7 g (P<0.05) ipsilateral to the spinal cord hemisection and from 5.75±1.41 g to 3.38±0.9 g (P<0.01) contralateral to the spinal cord hemisection (FIG. 6A) measured 10-15 minutes after drug administration. Intrathecal phaclofen reduced the mechanical threshold to 3.6±0.78 g (P<0.05) ipsilateral to the spinal cord hemisection and 4.05±0.75 g (P<0.05) contralateral to the spinal cord hemisection (FIG. 6A). The thermal withdrawal latency was reduced from 9.28±1.39 s to 7.23±1.21 s (P<0.05) ipsilateral, and from 9.56±1.5 s to 7.41±1.29 s P<0.05) contralateral by administration of bicuculline and to 7.54±1.16 s (P<0.05) ipsilateral, 7.66±1.24 s (P<0.05) contralateral by administration of phaclofen (FIG. 6B). In each case the effect of the drug was measured at the peak effect 30 minutes after drug administration. One hour after inoculation there was no longer any detectable drug effect. There were no significant changes in either mechanical threshold or thermal latency in spinal cord hemisected rats inoculated with Q0ZHG and treated with bicuculline or phaclofen at the same doses.

EXAMPLE 7

This example demonstrates that transduction of cells with a GAD vector reduces CGRP immunoreactivity in the dorsal horn.

Figure 7:
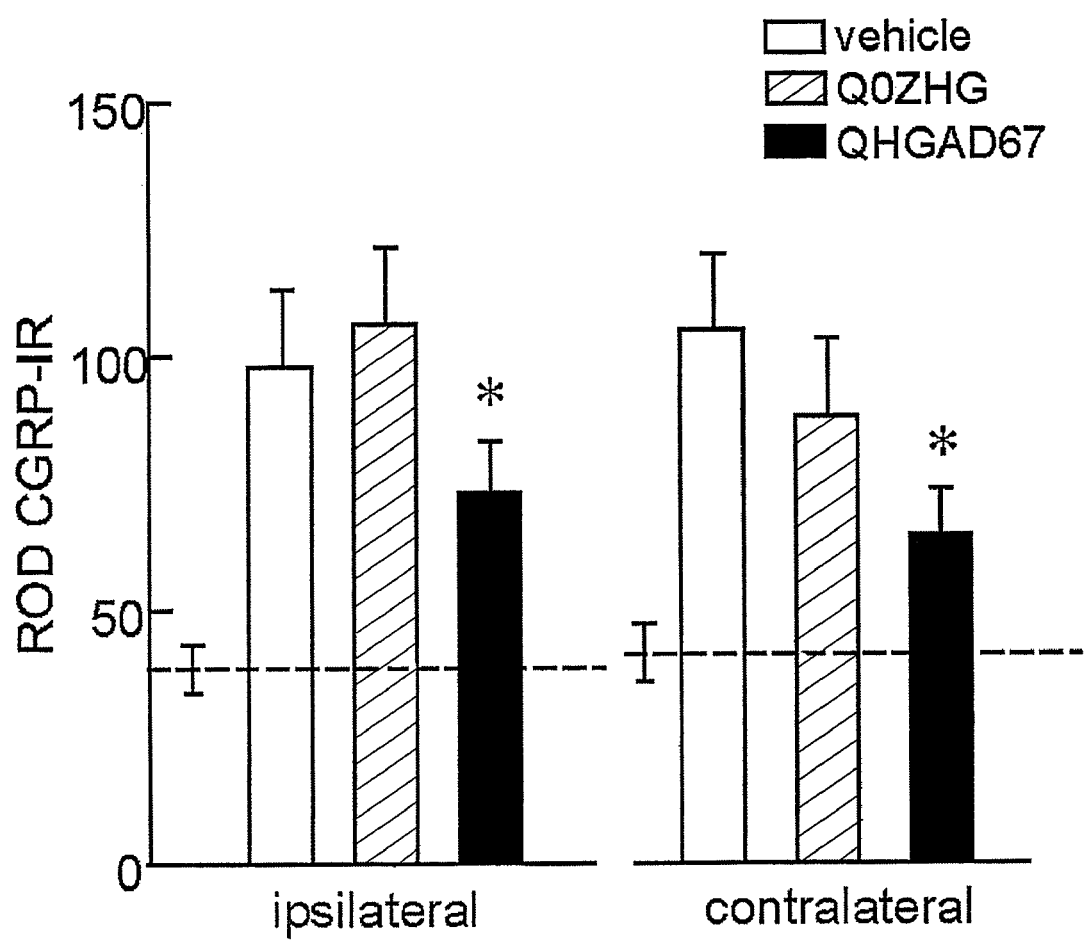
FIG. 7 is a histogram of the relative optical density measurements of CGRP-like immunoreactivity in dorsal horn. The relative optical density measurements were taken from a series of six continuous sections in the L5 segment of each animal. The dotted line indicates that the density of CGRP-IR in normal spinal cord is increased substantially both ipsilateral and contralateral to T13 hemisection in animals inoculated with vehicle or Q0ZHG, and inoculation with QHGAD67 significantly attenuates this increase. Means±SEM, n=6, *$P<0.051$ compared to vehicle or Q0ZHG.

In sham-operated animals, CGRP immunoreactivity at the L5 segment was weak, confined largely to laminae I and II within the superficial dorsal horn of the spinal cord bilaterally. One week after left T13 hemisection, CGRP immunoreactivity was increased and staining could be detected extending into laminae III and IV of dorsal spinal cord bilaterally. In spinal cord hemisected rats 1 week after inoculation of QHGAD67 in both hindpaws, CGRP-like immunoreactivity was reduced (76.5±13.3 OD unit ipsilateral, 63.6±12.4 OD unit contralateral) compared to spinal cord hemisected rats inoculated with Q0ZHG (107.3±22.4 OD unit ipsilateral, 86±23.5 unit contralateral, P<0.0-5) or vehicle-treated animals (96.7±21.8 OD unit ipsilateral, 104.6±22.6 OD unit contralateral, P<0.05). There was no significant difference in staining between Q0ZHG-inoculated and vehicle-treated animals (FIG. 7).

The distribution of GAD protein in unlesioned transduced animals and CGRP peptide in lesioned transduced animals was determined by immunohistochemistry. Rats were perfused intracardially with 4% paraformaldehyde in 0.1 M phosphate buffer, the L5 segment of spinal cord and attached roots removed, postfixed in the same solution for two hours, and cryoprotected with 30% sucrose in PBS for two days. Twenty-micrometer cryostat sections were thaw mounted onto cold Superfrost microscope slides (Fisher, Pittsburgh, Pa., USA) and incubated overnight at 4° C. with rabbit anti-GAD67 (1:2000, Chemicon) or rabbit anti-CGRP (1:500, PLI, San Carlos, Calif., USA) followed by fluorescent anti-rabbit IgG (Alexa Fluor 594, 1:500, Molecular Probes, Eugene, Oreg., USA) for two hours at room temperature. Fluorescent images were captured by confocal microscopy (Diagnostic Instruments, Sterling Heights, Mich., USA).

EXAMPLE 8

This example demonstrates that transfer of the gene encoding GAD to dorsal root ganglion using a herpes simplex virus vector attenuates peripheral neuropathic pain.

Male Sprague-Dawley rats weighing 225 to 250 gm underwent selective L5 SNL (as described in Hao et al., Pain; 102:135-42 (2003)). One week after SNL, 30 μl of vector (either QHGAD67 or Q0ZHG, $4 \times 10^8$ plaque-forming units per milliliter) was injected subcutaneously in the plantar surface of the left hind paw, ipsilateral to the ligation. Mechanical allodynia induced by SNL was determined by assessing the response of paw withdrawal to von Frey hairs of graded tensile strength (see Hao et al., supra, and Chaplan et al., J Neurosci Methods, 53:55-63 (1994)) with a tactile stimulus producing a 50% likelihood of withdrawal determined using the up-down method (see Dixon et al., Annu Rev Pharmacol Toxicol; 20:441-62 (1980)) Thermal hyperalgesia was determined using a Hargreaves apparatus (as described in Hargreaves et al., Pain; 32:77-88 (1988)) recording the time to withdrawal from a radiant thermal stimulus positioned directly under the hind paw.

Figure 11:
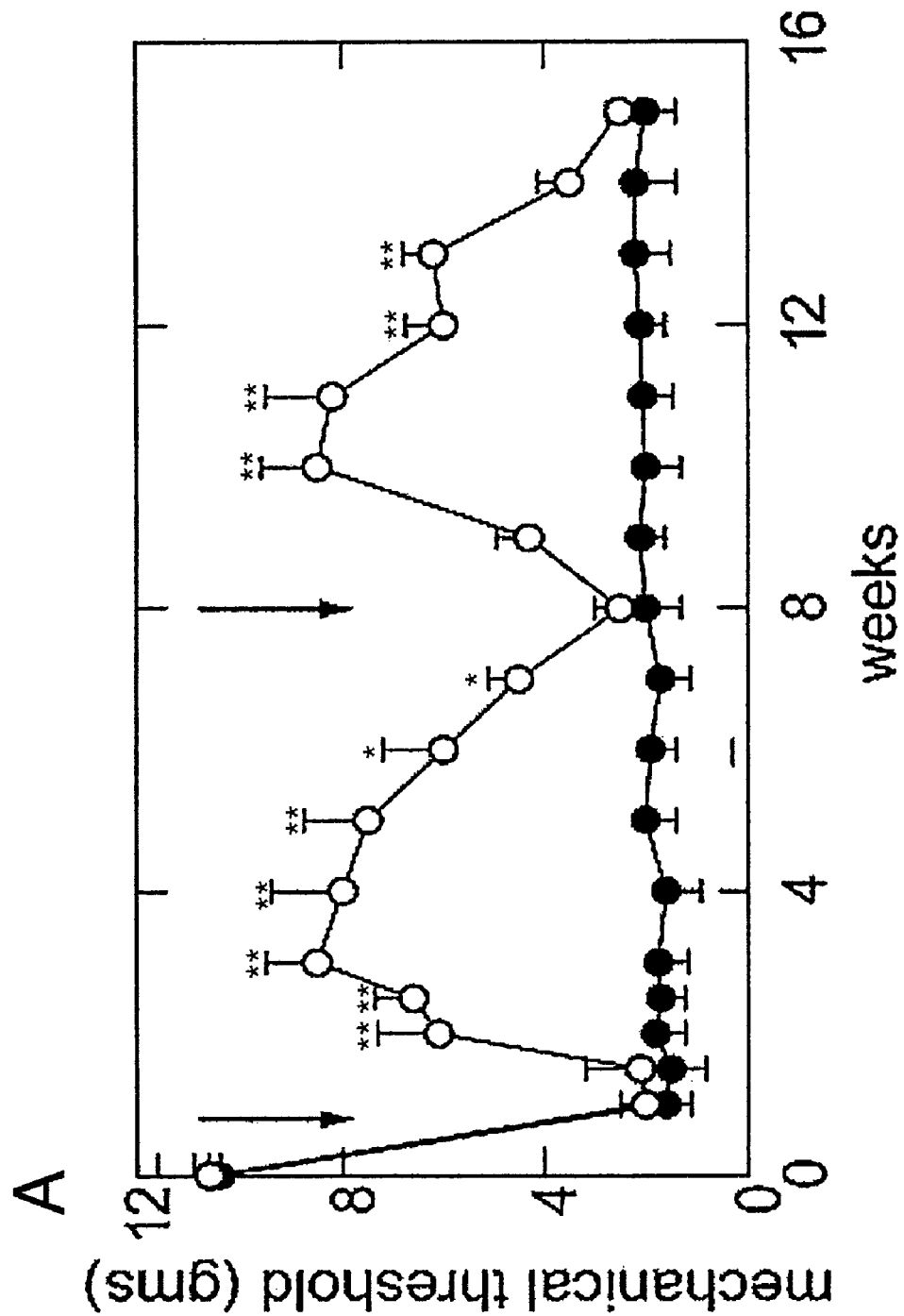
FIGS. 11(a) and 11(b) depict data demonstrating Antinociceptive effect of QOGAD67 in neuropathic pain. (A) L5 spinal nerve ligation (SNL) caused a significant decrease in the threshold to tactile stimulation, which persisted for more than 4 months. Subcutaneous inoculation of QHGAD67 (arrow) produced an antiallodynic effect reflected in an increase in the mechanical threshold. Reinoculation of QHGAD67 7 weeks after the initial inoculation (arrow) reestablished the antiallodynic effect. Results are expressed as mean±standard error of the mean. (open circles) QHGAD67; (closed circles) QOZHG; *$p<0.05$; **$p<0.01$; n=8 animals per group. (B) L5 SNL also caused a significant thermal hyperalgesia, which persisted for 6 weeks. Inoculation with QHGAD67 (arrow), but not QOZHG, reversed the thermal hyperalgesia induced by spinal nerve injury. *$p<0.05$; $p<0.01$ versus QOZHG-inoculated; n=8 animals per group. The statistical significances of the differences were determined by analysis of variance
Figure 11:
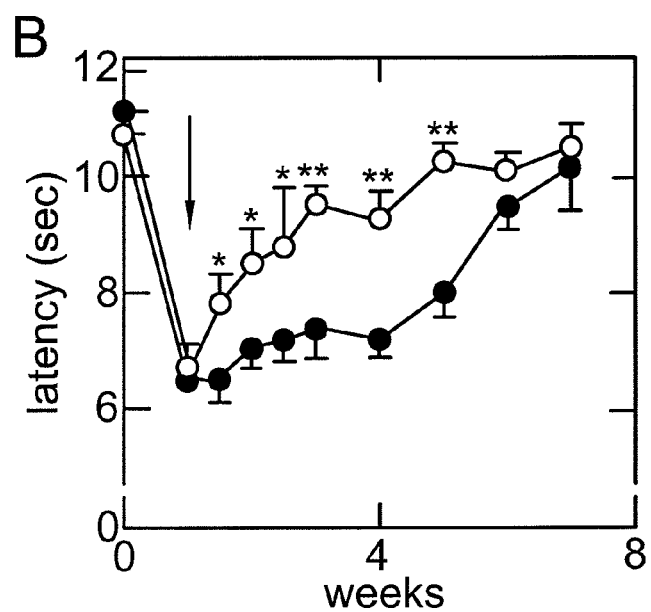

After L5 SNL, rats displayed a significant decrease in the magnitude of the mechanical stimulus necessary to evoke a brisk withdrawal response to von Frey hair stimulation (FIG. 11A) and a significant reduction in latency to withdraw from a heat stimulus (thermal hyperalgesia; see FIG. 11B). Rats inoculated with QH-GAD67 showed a statistically significant increase in mechanical threshold beginning 1 week after inoculation. The antiallodynic effect of QHGAD67-mediated GABA expression was sustained and continuous, lasting 5 to 6 weeks and peaking at 2 weeks after inoculation (see FIG. 11A). The peak value of mechanical threshold, 8.6 gm, was close to the preoperative value. By 7 weeks after inoculation, the antiallodynic effect of vector transduction disappeared, and the mechanical threshold of QHGAD67-injected rats was identical to that of control rats. Reinoculation into the same paw with the same dose of QHGAD67 reestablished the antiallodynic effect (see FIG. 11A). SNL induced a decrease in the thermal latency from 10.7 to 6.5 seconds, which lasted 3 weeks before gradually recovery. Rats inoculated with QHGAD67 showed a statistically significant increase in thermal latency in the ipsilateral paw beginning 1 week after inoculation (see FIG. 11B), an effect that was sustained and continuous, lasting 3 to 4 weeks (see FIG. 11B). Sham-operated animals had no change in mechanical thresh-old or thermal latency.

Figure 12:
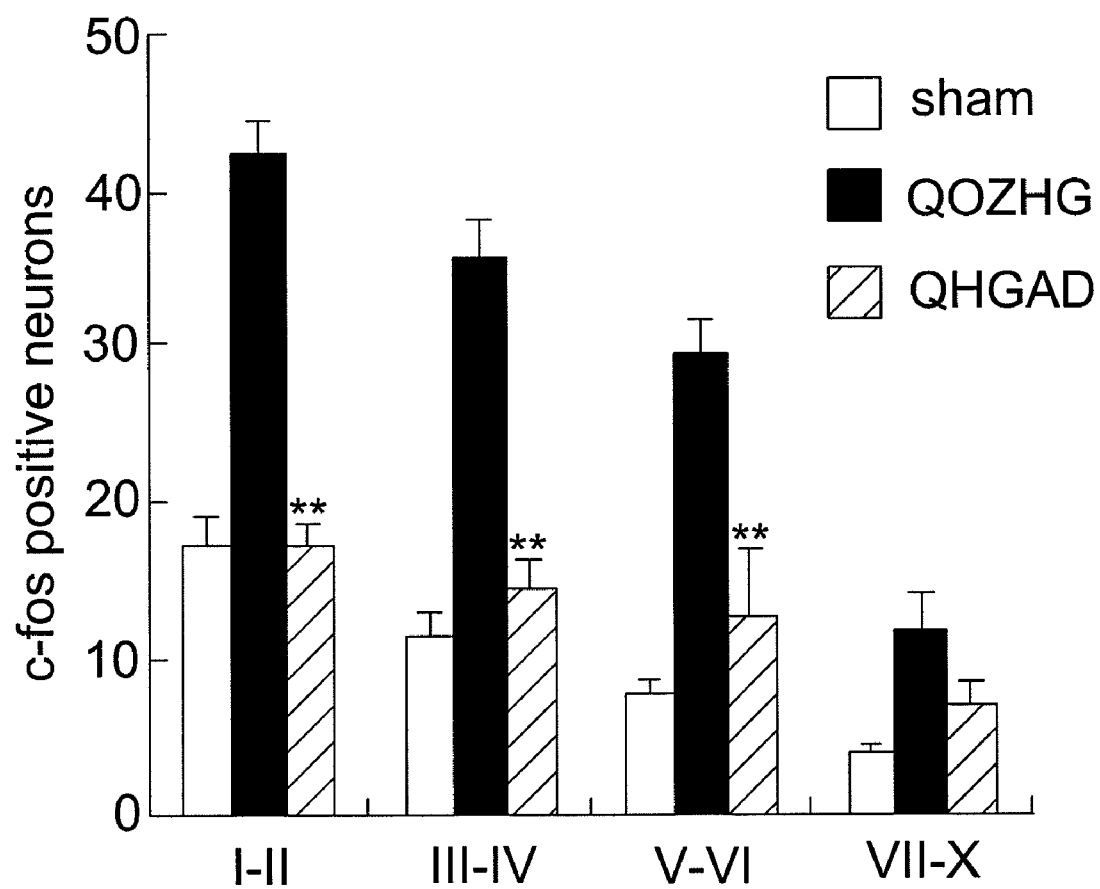
FIG. 12 is a histogram depicting data concerning the effect of QHGAD67 on Fos-LI in dorsal horn. Fos-LI in dorsal horn induced by 10 minutes of gentle tactile stimulation was markedly increased in rats inoculated with QOZHG 1 week after spinal nerve ligation (SNL) and tested 2 weeks later (3 weeks after SNL). This increase was blocked in rats with SNL that had been inoculated with QHGAD67 1 week after SNL and tested 2 weeks later (3 weeks after SNL), and it was found in laminae I-VI of dorsal horn. Results are expressed as mean±standard error of the mean. $p<0.01$; n=5 animals per group. The difference between sham-operated and SNL animals inoculated with QOZHG was also statistically significant ($p<0.01$).
Figure 13:
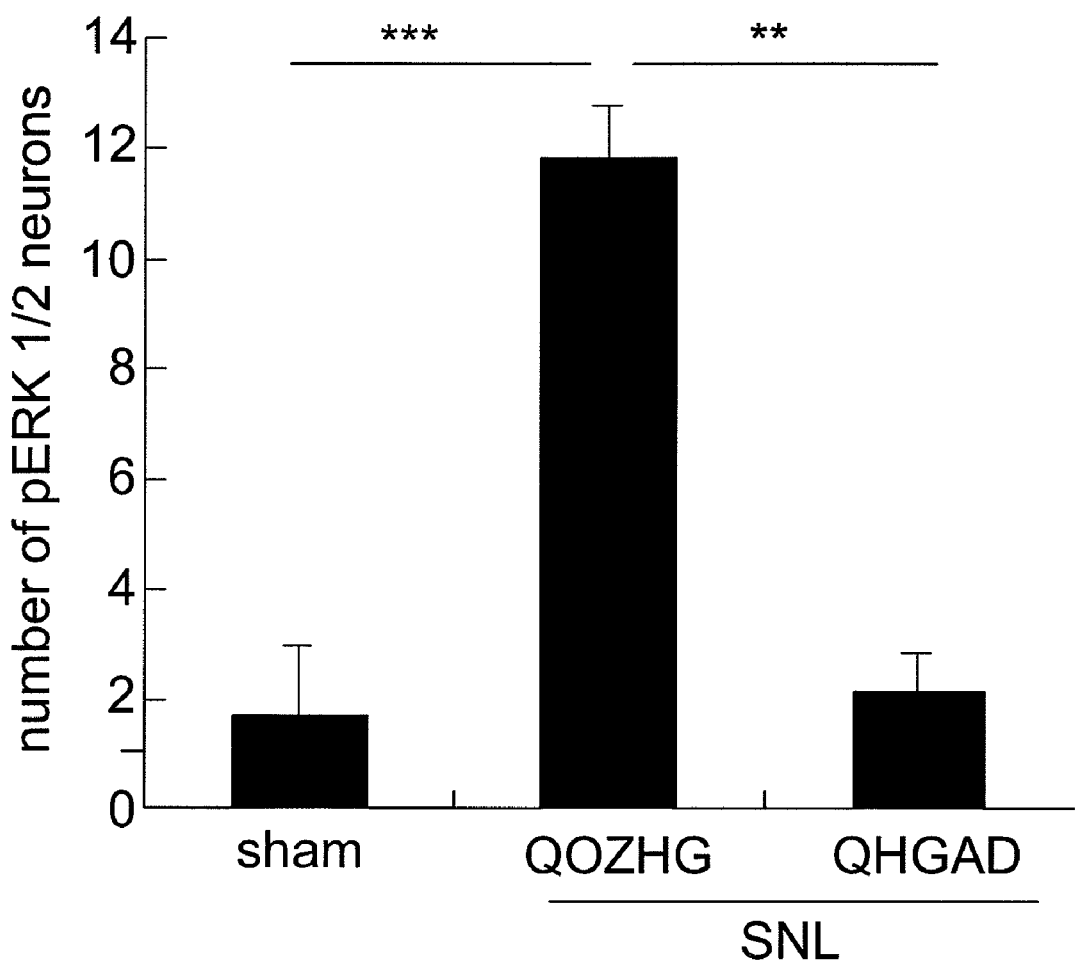
FIG. 13 graphically depicts data concerning the effect of QHGAD67 on the phosphorylated extracellular signal-regulated kinase 1 and 2 (p-ERK1/2) expression in dorsal horn. Results are expressed as mean±standard error of the mean. $p<0.01$; *$p<0.001$; n=5 animals per group.

Expression of c-Fos and phosphorylated extracellular signal-regulated kinase 1 and 2 (p-ERK1/2) induced by gentle touch is one indirect biological marker of nociceptive processes (Catheline et al., Pain; 92:389-98 (2001)). Three weeks after SNL, gentle touch was applied once every 4 seconds for 10 minutes, with the flat surface of the experimenter's thumb to the rat's paw, and the number of immunoreactive cells (anti-c-Fos or anti-p-ERK1/2 antibodies; Santa Cruz Biotechnology, Santa Cruz, Calif.) detected avidin-biotin horseradish peroxidase followed by nickel-enhanced diaminobenzidine (Vector Laboratories, Bur-lingame, Calif.). 12 The number of Fos-LI-positive neurons was substantially increased ipsilateral to SNL compared with sham-operated control rats, and inoculation of vector QHGAD67 significantly reduced the number Fos-LI positive neurons in laminae I-VI (see FIG. 12). p-ERK1/2 expression in laminae I and II was also increased in rats after gentle touch stimulation with SNL, and that increase was blocked in animals inoculated with QHGAD67. p-ERK was not induced by 10 minutes of gentle tactile stimulation in sham-operated animals but it was substantially induced after spinal nerve ligation (SNL) in animals inoculated with QOZHG. Touch-induced expression of p-ERK1/2 was suppressed in animals inoculated with QHGAD67, confirmed by counts of p-ERK1/2-positive neurons in the dorsal horn (FIG. 13).

These results demonstrate that subcutaneous inoculation of an HSV vector expressing GAD to transduce DRG in vivo attenuated the behavioral manifestations of mechanical allodynia and thermal hyperalgesia in a model of peripheral neuropathic pain; the effect on behavior was confirmed by histological measures showing a block in the induction of expression of c-Fos and p-ERK1/2 in the ipsilateral spinal dorsal horn.

DISCUSSION

The lateral hemisection of a laboratory rat's spinal cord at T13 produces bilateral SCI pain related behavior below the lesion in both hind limbs ("the SCI model"). The SCI pain related behavior is manifested as mechanical allodynia and thermal hyperalgesia. This phenomenon is accompanied by bilateral spinal cord reorganization. In the above mentioned experiments, this SCI model was used to examine the effects of the local production and release of GABA due to a GAD vector mediated gene transfer to the lumbar DRG in alleviating some of the manifestations of SCI pain.

DRG neurons were transduced with a HSV vector encoding for GAD ("the GAD vector"). These transduced DRG neurons expressed GAD in vitro and in vivo. The expression of GAD in these cells resulted in the release of GABA. In the laboratory rats subjected to lateral hemisection of the spinal cord at T13 followed by subcutaneous inoculation with the GAD vector, regional GABA release from transduced DRG neurons reduced mechanical allodynia and thermal hyperalgesia in the hind limbs. This effect could be reversed by either $GABA_A$ or $GABA_B$ receptor antagonists administered at doses that did not alter nociception in normal animals or in laboratory rats subjected to lateral hemisection of the spinal cord at T13 without subcutaneous inoculation with the GAD vector. Moreover, GAD vector mediated GABA release also attenuated the increase in CGRP immunoreactivity in the lumbar dorsal horn that occurs after SCI. Therefore, the inventive method involving GAD vector mediated gene transfer to DRG can effectively be used to treat below level neuropathic SCI pain.

Release of GABA from primary DRG neurons transduced in vitro with the GAD vector was not increased in a medium containing 60 mM $K^+$ and was unaffected by removal of $Ca^{2+}$ from the medium suggesting that GABA release is not vesicular, but occurs constitutively, perhaps through reversal of the GABA transporter. Although the amount of GABA released from nerve terminals in vivo was sufficient to elevate GABA levels in microdialysate of the dorsal horn significantly, there was no evidence of motor weakness in these animals, suggesting that transgene mediated GABA release was limited to the dorsal horn. This would be consistent with the observation that animals transduced by subcutaneous inoculation of the proenkephalin expressing HSV vector acquired an analgesic effect that was limited to the limb ipsilateral to the inoculation.

In laboratory rats with uninjured spinal cords, tonic GABA-ergic inhibition of low threshold afferent inputs modulates sensory processing, and bicuculline block of GABA receptor function produces pain-related behavior. Electrophysiologic studies suggest that both $GABA_A$ and $GABA_B$ receptors contribute to the tonic modulation of nociceptive neurotransmission at the spinal cord level. Peripheral nerve injury results in a decrease in GABA levels in the dorsal horn and a reduction in the primary afferent evoked inhibitory post synaptic currents in the dorsal horn after partial nerve injury. However, whether these phenomena result from a loss of GABA-ergic interneurons or a desensitization of GABA receptors as found in central sensitization has not been fully established. A transient reduction in GABA immunoreactivity has been reported in the lumbar spinal cord after photochemical induction of spinal ischemia, but previous studies have not examined GABA immunoreactivity below the level of hemisection. Nonetheless, constitutive delivery of GABA to the dorsal horn below the level of the hemisection as a result of GAD vector transduction of DRG neurons reduced behavioral measures of mechanical allodynia and thermal hyperalgesia after SCI. This indicates that SCI pain is susceptible to modulation by GABA.

The effect of baclofen on central neurogenic pain has been assessed in several trials with generally positive results in brief trials, but with less remarkable long-term relief. Intrathecal administration of baclofen partially alleviates chronic mechanical and cold allodynia in an ischemia model of SCI. In a chronic constriction injury model of neuropathic pain, intrathecal transplantation of GABA-releasing cells reverses some of the manifestations of neuropathic pain. It has been discovered that the pain-relieving effects of GAD vector mediated GABA release were continuous over the course of several weeks.

The amount of GABA release over time was not measured. However, it was observed that the reinoculation of the GAD vector after the analgesic effect had waned reestablished the reduction in mechanical allodynia and thermal hyperalgesia. This observation demonstrates that the loss of therapeutic effect was not due to the development of tolerance, but to a reduction in gene expression. This is consistent with the findings of previous studies that examined vectors in which transgene expression was driven by transiently active human cytomegalovirus immediate early promoter (HCMV IEp).

There are no "objective" measures of pain and pain relief. However, measurements of the increase in the amount of CGRP immunoreactivity in spinal cord segments below the level of injury in the SCI model have been used to measure pain and pain relief in the laboratory. Unfortunately, little is known about the phenomena of increased spinal cord CGRP in the SCI model. The mechanisms responsible for the increase in below-level CGRP have not been defined. It is not known whether the increase in immunoreactivity correlates with increased release on turnover of CGRP. It is also not known whether CGRP plays any role in the SCI pain phenomenon or occurs as an epiphenomenon of SCI. Nonetheless, the increase in CGRP that occurs after SCI in these studies serves as a histologic correlate to the behavioral measures of pain analogous to the increase in c-fos immunoreactivity induced by nonnoxious touch in the spinal cord nerve ligation model of peripheral neuropathic pain. Therefore, measurements of CGRP can be used to determine the effect of GAD vectors in treating SCI pain. While not wishing to be bound to any particular theory, because CGRP is located in the unmyelinated and thinly myelinated afferents that project principally to laminae I, II, and V, of the dorsal horn, the increase in CGRP is believed to result from the sprouting of primary afferents. The mechanism through which GABA release from GAD transduced cells prevents the increase in CGRP expression is not known.

From the foregoing, in accordance with the invention, a nonreplicating HSV vector designed to express human glutamic acid decarboxylase (GAD) was successfully constructed, and this vector was used to treat SCI pain and also peripheral neuropathic pain. These examples demonstrate that the inventive method involving the use of a gene transfer approach can be used to transduce DRG neurons through peripheral inoculation to release GABA in the dorsal horn. These examples also demonstrate that the inventive method involving gene transfer using the GAD vector reduces below-level mechanical allodynia and thermal hyperalgesia after SCI. The ability to deliver the GAD vector by subcutaneous inoculation is an attractive feature of the inventive approach to treat SCI pain and also peripheral neuropathic pain.

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.))

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A cell line that contains herpes simplex virus (HSV) ICP4, ICP27, and UL55 genes, wherein the cell line supports the replication of an HSV vector comprising deletions in ICP4, ICP27, and UL55 genes, wherein the vector does not comprise a deletion in UL56.

2. A combination comprising the cell of claim 1 and an HSV vector comprising deletions in ICP4, ICP27, and UL55 genes, wherein the ICP4, ICP27, and UL55 genes within the cell share no homology with the vector DNA.

3. The combination of claim 2, wherein the vector comprises a transgene.

* * * * *